(12) United States Patent
Joseph et al.

(10) Patent No.: US 11,892,450 B2
(45) Date of Patent: Feb. 6, 2024

(54) EVALUATION, ASSAYS AND TREATMENT OF PKAL-MEDIATED DISORDERS

(71) Applicant: Takeda Pharmaceutical Company Limited, Osaka (JP)

(72) Inventors: Kusumam Joseph, Mt. Pleasant, SC (US); Allen P. Kaplan, Charleston, SC (US)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 16/881,911

(22) Filed: May 22, 2020

(65) Prior Publication Data

US 2020/0393464 A1 Dec. 17, 2020

Related U.S. Application Data

(62) Division of application No. 14/761,671, filed as application No. PCT/US2014/012090 on Jan. 17, 2014, now Pat. No. 10,690,670.

(60) Provisional application No. 61/754,600, filed on Jan. 20, 2013.

(51) Int. Cl.
| | | |
|---|---|---|
| G01N 33/53 | (2006.01) | |
| G01N 33/573 | (2006.01) | |
| C12Q 1/37 | (2006.01) | |
| G01N 33/68 | (2006.01) | |
| C07K 16/38 | (2006.01) | |
| C07K 14/435 | (2006.01) | |
| C07K 16/40 | (2006.01) | |

(52) U.S. Cl.
CPC ......... *G01N 33/573* (2013.01); *C07K 14/435* (2013.01); *C07K 16/38* (2013.01); *C07K 16/40* (2013.01); *C12Q 1/37* (2013.01); *G01N 33/6893* (2013.01); *C07K 2317/21* (2013.01); *C07K 2317/76* (2013.01); *G01N 2333/4706* (2013.01); *G01N 2333/8121* (2013.01); *G01N 2333/96455* (2013.01); *G01N 2333/96458* (2013.01); *G01N 2800/32* (2013.01); *G01N 2800/52* (2013.01); *G01N 2800/70* (2013.01)

(58) Field of Classification Search
None
See application file for complete search history.

(56) References Cited

U.S. PATENT DOCUMENTS

| | | | |
|---|---|---|---|
| 4,849,353 A | 7/1989 | Harpel | |
| 7,998,679 B2 | 8/2011 | Jacobs et al. | |
| 10,690,670 B2 | 6/2020 | Joseph et al. | |
| 2007/0231790 A1 | 10/2007 | Su | |
| 2009/0064350 A1 | 3/2009 | Dewald | |
| 2010/0119512 A1 | 5/2010 | Feener et al. | |
| 2011/0140706 A1 | 6/2011 | Groves et al. | |
| 2012/0058130 A1 | 3/2012 | Donal | |
| 2012/0082676 A1 | 4/2012 | Ghebrehiwet | |
| 2012/0201756 A1 | 8/2012 | Sexton | |
| 2012/0328517 A1 | 12/2012 | Markland et al. | |
| 2014/0335023 A1* | 11/2014 | Sexton | A61P 1/00 424/139.1 |

FOREIGN PATENT DOCUMENTS

| | | |
|---|---|---|
| CN | 1142984 A | 2/1997 |
| CN | 1368886 A | 9/2002 |
| CN | 1867679 A | 11/2006 |
| CN | 101023349 A | 8/2007 |
| CN | 101137412 A | 3/2008 |
| CN | 101166762 A | 4/2008 |
| CN | 102216779 A | 10/2011 |
| CN | 102307594 A | 1/2012 |
| EP | 1598428 A1 | 11/2005 |
| JP | S57-94660 A | 6/1982 |
| JP | H3-179264 A | 8/1991 |
| JP | 2003-521914 A | 7/2003 |
| JP | 2005-509127 A | 4/2005 |
| JP | 2003-521914 A5 | 2/2008 |
| WO | WO 01/57079 A2 | 8/2001 |
| WO | WO 02/42775 A2 | 5/2002 |
| WO | WO 2006/091459 A2 | 8/2006 |
| WO | WO 2008/098720 A1 | 8/2008 |

OTHER PUBLICATIONS

Prince, Biomarkers 10 Supplement 1: S44-S49, 2005. (Year: 2005).*
Biomarkers Definitions Working Groups., Clin. Pharmacol. Ther. 69: 89-95, 2001. (Year: 2001).*
Attwood, Science 290:471-473, 2000. (Year: 2000).*
Skolnick et al., Trends in Biotech. 18: 34-39, 2000. (Year: 2000).*
D'Angelo et al., Many Routes to an Antibody Heavy-Chain CDR3: Necessary, Yet Insufficient, for Specific Binding (Frontiers in Immunology vol. 9, Article 395 Mar. 2018; doi:10.3389/fimmu.2018.00395. (Year: 2018).*
Xie et al., European Journal of Medicinal Chemistry 190 (2020) 112137; doi,org/10.1016/j.3jmech.2020.112137. (Year: 2020).*
Rudikoff et al., (Proc Natl Acad Sci USA 79: 1979-1983 (1982). (Year: 1982).*
Colman, Research in Immunology 145: 33-36, 1994. (Year: 1994).*
Kussie et al., J. Immunol. 152: 146-152, 1994. (Year: 1994).*
Chen et al., EMBO J., 14: 2784-2794, 1995. (Year: 1995).*

(Continued)

*Primary Examiner* — Michael Szperka
(74) *Attorney, Agent, or Firm* — Wolf, Greenfield & Sacks, P.C.

(57) ABSTRACT

The invention provides assay methods of detecting plasma protease CI inhibitor (C1-INH) that binds plasma kallikrein, Factor XII, or both, and uses thereof for identifying subjects at risk for or suffering from a pKal-me-diated or bradykinin-mediated disorder. Provided methods permit analysis of patients with plasma kallikrein-mediated angioedema (KMA), or other diseases mediated by pKal useful in the evaluation and treatment.

20 Claims, 4 Drawing Sheets

Specification includes a Sequence Listing.

(56) References Cited

OTHER PUBLICATIONS

Varga et al., rhC1INH: a new drug for the treatment of attacks in hereditary angioedema caused by C1-inhibitor deficiency. Expert Rev Clin Immunol. 2011;7(2):143-153. Epub Jan. 10, 2014.
Nuijens et al., Quantification of plasma factor XIIa-C1(-)-inhibitor and kallikrein-C1(-)-inhibitor complexes in sepsis. Blood. Dec. 1988;72(6):1841-8.
Attwood, Genomics. The Babel of bioinformatics. Science. Oct. 20, 2000; 290(5491): 471-3. doi: 10.1126/science.290.5491.471.
Bork, Current management options for hereditary angioedema. Curr Allergy Asthma Rep. Aug. 2012; 12(4): 273-280. doi: 10.1007/s11882-012-0273-4.
De Smet et al., Clearance of human native, proteinase-complexed, and proteolytically inactivated C1-inhibitor in rats. Blood. Jan. 1, 1993; 81(1): 56-61.
Govers-Riemslag et al., The plasma kallikrein-kinin system and risk of cardiovascular disease in men. J Thromb Haemost. Sep. 2007; 5(9): 1896-1903.
Kaplan et al., Assessment of Hageman Factor Activation in Human Plasma: Quantification of Activated Hageman Factor-C1 Inactivator Complexes by an Enzyme-Linked Differential Antibody Immunsorbent Assay. Blood. Sep. 1985; 66(3): 636-641.
Kenniston et al., Inhibition of plasma kallikrein by a highly specific active site blocking antibody. J Biol Chem. Aug. 22, 2014; 289(34): 23596-608. doi:10.1074/jbc.M114.569061. Epub Jun. 26, 2014.
Lewin et al., Studies of C1 Inactivator-Plasma Kallikrein Complexes in Purified Systems and in Plasma. Journal of Biological Chemistry. May 1983; 258(10): 6415-6421.
Nuijens et al., Detection of Activation of the Contact System of Coagulation In Vitro and In Vivo: Quantitation of Activated Hageman Factor-C1-Inhibitor and Kallikrein-C1-Inhibitor Complexes by Specific Radioimmunoassays. Thrombosis and Haemostasis. 1987; 58(2): 778-785.
Riedl, Hereditary angioedema therapy: kallikrein inhibition and bradykinin receptor antagonism. World Allergy Organ J. Sep. 2010; 3(9 Suppl): S34-S38. doi:10.1097/WOX.0b013e3181f20dbc.

Schneider et al., Critical role of kallikrein in hereditary angioedema pathogenesis: a clinical trial of ecallantide, a novel kallikrein inhibitor. J Allergy Clin Immunol. Aug. 2007; 120(2): 416-422. Epub Jun. 7, 2007.
Skolnick et al., From genes to protein structure and function: novel applications of computational approaches in the genomic era. Trends Biotechnol. Jan. 2000; 18(1): 34-9. doi: 10.1016/s0167-7799(99)01398-0.
Wagenaar-Bos et al., Functional C1-inhibitor diagnostics in hereditary angioedema: assay evaluation and recommendations. J Immunol Methods. Sep. 30, 2008; 338(1-2): 14-20. doi: 10.1016/j.jim.2008.06.004. Epub Jul. 23, 2008.
Waytes et al., Treatment of hereditary angioedema with a vapor-heated C1 inhibitor concentrate. N Engl J Med. Jun. 20, 1996; 334(25): 1630-1634.
Alsenz et al., Simplified methods for the purification, quantitation, and functional estimation of human complement C-1-inhibitor (C-1-INH) with a monoclonal anti-C-1-INH antibody. J Immunol Methods. Jan. 26, 1987;96(1):107-14. doi: 10.1016/0022-1759(87)90373-5.
Caballero et al., Consensus statement on the diagnosis, management, and treatment of angioedema mediated by bradykinin. Part II. Treatment, follow-up, and special situations. J Investig Allergol Clin Immunol. 2011;21(6):422-41.
No Author Listed], United States Court of Appeals for the Federal Circuit. *Erfindergemeinschaft Uropep GbR* v. *Eli Lilly and Company.* Appeal from the United States District Court for the Eastern District of Texas in No. 2:15-cv-01202-WCB, Circuit Judge William C. Bryson. Aug. 25, 2017. 83 pages.
Kolker, D., Antibodies and the written description requirement of 35 U.S.C.112(a). USPTO Biotechnology Chemical Pharmaceutical Customer Partnership Meeting. Sep. 17, 2020, 36 pages.
[No Author Listed], Hereditary Angioedema (HAE) Guidelines 2010. Homepage of the Japanese Association of Complement Research. 2010. https://square.umin.ac.jp/compl/common/images/diseaseinformation/hae/HAEGuideline2010.pdf [last accessed Nov. 8, 2023]. 5 pages.

* cited by examiner

SEQUENCE LISTING

```
<160> NUMBER OF SEQ ID NOS: 12

<210> SEQ ID NO 1
<211> LENGTH: 500
<212> TYPE: PRT
<213> ORGANISM: Homo sapiens

<400> SEQUENCE: 1

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Ser Pro Arg Val Leu Ser Asn Asn Ser Asp
```

```
                    245                 250                 255

Ala Asn Leu Glu Leu Ile Asn Thr Trp Val Ala Lys Asn Thr Asn Asn
                260                 265                 270

Lys Ile Ser Arg Leu Leu Asp Ser Leu Pro Ser Asp Thr Arg Leu Val
            275                 280                 285

Leu Leu Asn Ala Ile Tyr Leu Ser Ala Lys Trp Lys Thr Thr Phe Asp
        290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
370                 375                 380

Lys Leu Glu Met Ser Lys Phe Gln Pro Thr Leu Leu Thr Leu Pro Arg
                390                 395                 400
385

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ser Ala Ile Ser Val
        450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 2
<211> LENGTH: 619
<212> TYPE: PRT
<213> ORGANISM: Homo sapiens

<400> SEQUENCE: 2

Gly Cys Leu Thr Gln Leu Tyr Glu Asn Ala Phe Phe Arg Gly Gly Asp
1               5                   10                  15

Val Ala Ser Met Tyr Thr Pro Asn Ala Gln Tyr Cys Gln Met Arg Cys
            20                  25                  30

Thr Phe His Pro Arg Cys Leu Leu Phe Ser Phe Leu Pro Ala Ser Ser
        35                  40                  45

Ile Asn Asp Met Glu Lys Arg Phe Gly Cys Phe Leu Lys Asp Ser Val
    50                  55                  60

Thr Gly Thr Leu Pro Lys Val His Arg Thr Gly Ala Val Ser Gly His
65                  70                  75                  80

Ser Leu Lys Gln Cys Gly His Gln Ile Ser Ala Cys His Arg Asp Ile
                85                  90                  95

Tyr Lys Gly Val Asp Met Arg Gly Val Asn Phe Asn Val Ser Lys Val
            100                 105                 110
```

```
Ser Ser Val Glu Glu Cys Gln Lys Arg Cys Thr Ser Asn Ile Arg Cys
        115                 120                 125

Gln Phe Phe Ser Tyr Ala Thr Gln Thr Phe His Lys Ala Glu Tyr Arg
    130                 135                 140

Asn Asn Cys Leu Leu Lys Tyr Ser Pro Gly Gly Thr Pro Thr Ala Ile
145                 150                 155                 160

Lys Val Leu Ser Asn Val Glu Ser Gly Phe Ser Leu Lys Pro Cys Ala
                165                 170                 175

Leu Ser Glu Ile Gly Cys His Met Asn Ile Phe Gln His Leu Ala Phe
            180                 185                 190

Ser Asp Val Asp Val Ala Arg Val Leu Thr Pro Asp Ala Phe Val Cys
        195                 200                 205

Arg Thr Ile Cys Thr Tyr His Pro Asn Cys Leu Phe Phe Thr Phe Tyr
    210                 215                 220

Thr Asn Val Trp Lys Ile Glu Ser Gln Arg Asn Val Cys Leu Leu Lys
225                 230                 235                 240

Thr Ser Glu Ser Gly Thr Pro Ser Ser Ser Thr Pro Gln Glu Asn Thr
                245                 250                 255

Ile Ser Gly Tyr Ser Leu Leu Thr Cys Lys Arg Thr Leu Pro Glu Pro
            260                 265                 270

Cys His Ser Lys Ile Tyr Pro Gly Val Asp Phe Gly Gly Glu Glu Leu
        275                 280                 285

Asn Val Thr Phe Val Lys Gly Val Asn Val Cys Gln Glu Thr Cys Thr
    290                 295                 300

Lys Met Ile Arg Cys Gln Phe Phe Thr Tyr Ser Leu Leu Pro Glu Asp
305                 310                 315                 320

Cys Lys Glu Glu Lys Cys Lys Cys Phe Leu Arg Leu Ser Met Asp Gly
                325                 330                 335

Ser Pro Thr Arg Ile Ala Tyr Gly Thr Gln Gly Ser Ser Gly Tyr Ser
            340                 345                 350

Leu Arg Leu Cys Asn Thr Gly Asp Asn Ser Val Cys Thr Thr Lys Thr
        355                 360                 365

Ser Thr Arg Ile Val Gly Gly Thr Asn Ser Ser Trp Gly Glu Trp Pro
    370                 375                 380

Trp Gln Val Ser Leu Gln Val Lys Leu Thr Ala Gln Arg His Leu Cys
385                 390                 395                 400

Gly Gly Ser Leu Ile Gly His Gln Trp Val Leu Thr Ala Ala His Cys
                405                 410                 415

Phe Asp Gly Leu Pro Leu Gln Asp Val Trp Arg Ile Tyr Ser Gly Ile
            420                 425                 430

Leu Asn Leu Ser Asp Ile Thr Lys Asp Thr Pro Phe Ser Gln Ile Lys
        435                 440                 445

Glu Ile Ile Ile His Gln Asn Tyr Lys Val Ser Glu Gly Asn His Asp
    450                 455                 460

Ile Ala Leu Ile Lys Leu Gln Ala Pro Leu Asn Tyr Thr Glu Phe Gln
465                 470                 475                 480

Lys Pro Ile Cys Leu Pro Ser Lys Gly Asp Thr Ser Thr Ile Tyr Thr
                485                 490                 495

Asn Cys Trp Val Thr Gly Trp Gly Phe Ser Lys Glu Lys Gly Glu Ile
            500                 505                 510

Gln Asn Ile Leu Gln Lys Val Asn Ile Pro Leu Val Thr Asn Glu Glu
        515                 520                 525

Cys Gln Lys Arg Tyr Gln Asp Tyr Lys Ile Thr Gln Arg Met Val Cys
```

```
            530                 535                 540
Ala Gly Tyr Lys Glu Gly Gly Lys Asp Ala Cys Lys Gly Asp Ser Gly
545                 550                 555                 560

Gly Pro Leu Val Cys Lys His Asn Gly Met Trp Arg Leu Val Gly Ile
                565                 570                 575

Thr Ser Trp Gly Glu Gly Cys Ala Arg Arg Glu Gln Pro Gly Val Tyr
                580                 585                 590

Thr Lys Val Ala Glu Tyr Met Asp Trp Ile Leu Glu Lys Thr Gln Ser
                595                 600                 605

Ser Asp Gly Lys Ala Gln Met Gln Ser Pro Ala
                610                 615

<210> SEQ ID NO 3
<211> LENGTH: 638
<212> TYPE: PRT
<213> ORGANISM: Homo sapiens

<400> SEQUENCE: 3

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
                20                  25                  30

Gly Gly Asp Val Ala Ser Met Tyr Thr Pro Asn Ala Gln Tyr Cys Gln
            35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
                100                 105                 110

Arg Asp Ile Tyr Lys Gly Val Asp Met Arg Gly Val Asn Phe Asn Val
            115                 120                 125

Ser Lys Val Ser Ser Val Glu Glu Cys Gln Lys Arg Cys Thr Ser Asn
    130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
                180                 185                 190

Pro Cys Ala Leu Ser Glu Ile Gly Cys His Met Asn Ile Phe Gln His
            195                 200                 205

Leu Ala Phe Ser Asp Val Asp Val Ala Arg Val Leu Thr Pro Asp Ala
    210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Ser Thr Pro Gln
                260                 265                 270

Glu Asn Thr Ile Ser Gly Tyr Ser Leu Leu Thr Cys Lys Arg Thr Leu
            275                 280                 285
```

```
Pro Glu Pro Cys His Ser Lys Ile Tyr Pro Gly Val Asp Phe Gly Gly
    290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Lys Cys Lys Cys Phe Leu Arg Leu Ser
            340                 345                 350

Met Asp Gly Ser Pro Thr Arg Ile Ala Tyr Gly Thr Gln Gly Ser Ser
        355                 360                 365

Gly Tyr Ser Leu Arg Leu Cys Asn Thr Gly Asp Asn Ser Val Cys Thr
    370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
                405                 410                 415

His Leu Cys Gly Ser Leu Ile Gly His Gln Trp Val Leu Thr Ala
            420                 425                 430

Ala His Cys Phe Asp Gly Leu Pro Leu Gln Asp Val Trp Arg Ile Tyr
        435                 440                 445

Ser Gly Ile Leu Asn Leu Ser Asp Ile Thr Lys Asp Thr Pro Phe Ser
    450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
                485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
    515                 520                 525

Gly Glu Ile Gln Asn Ile Leu Gln Lys Val Asn Ile Pro Leu Val Thr
530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
                565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
    595                 600                 605

Gly Val Tyr Thr Lys Val Ala Glu Tyr Met Asp Trp Ile Leu Glu Lys
    610                 615                 620

Thr Gln Ser Ser Asp Gly Lys Ala Gln Met Gln Ser Pro Ala
625                 630                 635

<210> SEQ ID NO 4
<211> LENGTH: 638
<212> TYPE: PRT
<213> ORGANISM: Mus musculus

<400> SEQUENCE: 4

Met Ile Leu Phe Asn Arg Val Gly Tyr Phe Val Ser Leu Phe Ala Thr
1               5                   10                  15

Val Ser Cys Gly Cys Met Thr Gln Leu Tyr Lys Asn Thr Phe Phe Arg
                20                  25                  30
```

```
Gly Gly Asp Leu Ala Ala Ile Tyr Thr Pro Asp Ala Gln Tyr Cys Gln
         35                  40                  45

Lys Met Cys Thr Phe His Pro Arg Cys Leu Leu Phe Ser Phe Leu Ala
 50                  55                  60

Val Thr Pro Pro Lys Glu Thr Asn Lys Arg Phe Gly Cys Phe Met Lys
 65                  70                  75                  80

Glu Ser Ile Thr Gly Thr Leu Pro Arg Ile His Arg Thr Gly Ala Ile
                 85                  90                  95

Ser Gly His Ser Leu Lys Gln Cys Gly His Gln Ile Ser Ala Cys His
                100                 105                 110

Arg Asp Ile Tyr Lys Gly Leu Asp Met Arg Gly Ser Asn Phe Asn Ile
            115                 120                 125

Ser Lys Thr Asp Asn Ile Glu Glu Cys Gln Lys Leu Cys Thr Asn Asn
        130                 135                 140

Phe His Cys Gln Phe Phe Thr Tyr Ala Thr Ser Ala Phe Tyr Arg Pro
145                 150                 155                 160

Glu Tyr Arg Lys Lys Cys Leu Leu Lys His Ser Ala Ser Gly Thr Pro
                165                 170                 175

Thr Ser Ile Lys Ser Ala Asp Asn Leu Val Ser Gly Phe Ser Leu Lys
            180                 185                 190

Ser Cys Ala Leu Ser Glu Ile Gly Cys Pro Met Asp Ile Phe Gln His
        195                 200                 205

Ser Ala Phe Ala Asp Leu Asn Val Ser Gln Val Ile Thr Pro Asp Ala
210                 215                 220

Phe Val Cys Arg Thr Ile Cys Thr Phe His Pro Asn Cys Leu Phe Phe
225                 230                 235                 240

Thr Phe Tyr Thr Asn Glu Trp Glu Thr Glu Ser Gln Arg Asn Val Cys
                245                 250                 255

Phe Leu Lys Thr Ser Lys Ser Gly Arg Pro Ser Pro Pro Ile Pro Gln
            260                 265                 270

Glu Asn Ala Ile Ser Gly Tyr Ser Leu Leu Thr Cys Arg Lys Thr Arg
        275                 280                 285

Pro Glu Pro Cys His Ser Lys Ile Tyr Ser Gly Val Asp Phe Glu Gly
    290                 295                 300

Glu Glu Leu Asn Val Thr Phe Val Gln Gly Ala Asp Val Cys Gln Glu
305                 310                 315                 320

Thr Cys Thr Lys Thr Ile Arg Cys Gln Phe Phe Ile Tyr Ser Leu Leu
                325                 330                 335

Pro Gln Asp Cys Lys Glu Glu Gly Cys Lys Cys Ser Leu Arg Leu Ser
            340                 345                 350

Thr Asp Gly Ser Pro Thr Arg Ile Thr Tyr Gly Met Gln Gly Ser Ser
        355                 360                 365

Gly Tyr Ser Leu Arg Leu Cys Lys Leu Val Asp Ser Pro Asp Cys Thr
    370                 375                 380

Thr Lys Ile Asn Ala Arg Ile Val Gly Gly Thr Asn Ala Ser Leu Gly
385                 390                 395                 400

Glu Trp Pro Trp Gln Val Ser Leu Gln Val Lys Leu Val Ser Gln Thr
                405                 410                 415

His Leu Cys Gly Gly Ser Ile Ile Gly Arg Gln Trp Val Leu Thr Ala
            420                 425                 430

Ala His Cys Phe Asp Gly Ile Pro Tyr Pro Asp Val Trp Arg Ile Tyr
        435                 440                 445
```

```
Gly Gly Ile Leu Ser Leu Ser Glu Ile Thr Lys Glu Thr Pro Ser Ser
            450                 455                 460

Arg Ile Lys Glu Leu Ile Ile His Gln Glu Tyr Lys Val Ser Glu Gly
465                 470                 475                 480

Asn Tyr Asp Ile Ala Leu Ile Lys Leu Gln Thr Pro Leu Asn Tyr Thr
                485                 490                 495

Glu Phe Gln Lys Pro Ile Cys Leu Pro Ser Lys Ala Asp Thr Asn Thr
            500                 505                 510

Ile Tyr Thr Asn Cys Trp Val Thr Gly Trp Gly Tyr Thr Lys Glu Gln
            515                 520                 525

Gly Glu Thr Gln Asn Ile Leu Gln Lys Ala Thr Ile Pro Leu Val Pro
            530                 535                 540

Asn Glu Glu Cys Gln Lys Lys Tyr Arg Asp Tyr Val Ile Asn Lys Gln
545                 550                 555                 560

Met Ile Cys Ala Gly Tyr Lys Glu Gly Gly Thr Asp Ala Cys Lys Gly
                565                 570                 575

Asp Ser Gly Gly Pro Leu Val Cys Lys His Ser Gly Arg Trp Gln Leu
            580                 585                 590

Val Gly Ile Thr Ser Trp Gly Glu Gly Cys Gly Arg Lys Asp Gln Pro
            595                 600                 605

Gly Val Tyr Thr Lys Val Ser Glu Tyr Met Asp Trp Ile Leu Glu Lys
            610                 615                 620

Thr Gln Ser Ser Asp Val Arg Ala Leu Glu Thr Ser Ser Ala
625                 630                 635

<210> SEQ ID NO 5
<211> LENGTH: 638
<212> TYPE: PRT
<213> ORGANISM: Rattus norvegicus

<400> SEQUENCE: 5

Met Ile Leu Phe Lys Gln Val Gly Tyr Phe Val Ser Leu Phe Ala Thr
1               5                   10                  15

Val Ser Cys Gly Cys Leu Ser Gln Leu Tyr Ala Asn Thr Phe Phe Arg
            20                  25                  30

Gly Gly Asp Leu Ala Ala Ile Tyr Thr Pro Asp Ala Gln His Cys Gln
            35                  40                  45

Lys Met Cys Thr Phe His Pro Arg Cys Leu Leu Phe Ser Phe Leu Ala
            50                  55                  60

Val Ser Pro Thr Lys Glu Thr Asp Lys Arg Phe Gly Cys Phe Met Lys
65                  70                  75                  80

Glu Ser Ile Thr Gly Thr Leu Pro Arg Ile His Arg Thr Gly Ala Ile
                85                  90                  95

Ser Gly His Ser Leu Lys Gln Cys Gly His Gln Leu Ser Ala Cys His
            100                 105                 110

Gln Asp Ile Tyr Glu Gly Leu Asp Met Arg Gly Ser Asn Phe Asn Ile
            115                 120                 125

Ser Lys Thr Asp Ser Ile Glu Glu Cys Gln Lys Leu Cys Thr Asn Asn
130                 135                 140

Ile His Cys Gln Phe Phe Thr Tyr Ala Thr Lys Ala Phe His Arg Pro
145                 150                 155                 160

Glu Tyr Arg Lys Ser Cys Leu Leu Lys Arg Ser Ser Ser Gly Thr Pro
                165                 170                 175

Thr Ser Ile Lys Pro Val Asp Asn Leu Val Ser Gly Phe Ser Leu Lys
            180                 185                 190
```

```
Ser Cys Ala Leu Ser Glu Ile Gly Cys Pro Met Asp Ile Phe Gln His
        195                 200                 205

Phe Ala Phe Ala Asp Leu Asn Val Ser His Val Val Thr Pro Asp Ala
        210                 215                 220

Phe Val Cys Arg Thr Val Cys Thr Phe His Pro Asn Cys Leu Phe Phe
225                 230                 235                 240

Thr Phe Tyr Thr Asn Glu Trp Glu Thr Glu Ser Gln Arg Asn Val Cys
                245                 250                 255

Phe Leu Lys Thr Ser Lys Ser Gly Arg Pro Ser Pro Ile Ile Gln
        260                 265                 270

Glu Asn Ala Val Ser Gly Tyr Ser Leu Phe Thr Cys Arg Lys Ala Arg
        275                 280                 285

Pro Glu Pro Cys His Phe Lys Ile Tyr Ser Gly Val Ala Phe Glu Gly
        290                 295                 300

Glu Glu Leu Asn Ala Thr Phe Val Gln Gly Ala Asp Ala Cys Gln Glu
305                 310                 315                 320

Thr Cys Thr Lys Thr Ile Arg Cys Gln Phe Phe Thr Tyr Ser Leu Leu
                325                 330                 335

Pro Gln Asp Cys Lys Ala Glu Gly Cys Lys Cys Ser Leu Arg Leu Ser
        340                 345                 350

Thr Asp Gly Ser Pro Thr Arg Ile Thr Tyr Glu Ala Gln Gly Ser Ser
        355                 360                 365

Gly Tyr Ser Leu Arg Leu Cys Lys Val Val Glu Ser Ser Asp Cys Thr
        370                 375                 380

Thr Lys Ile Asn Ala Arg Ile Val Gly Gly Thr Asn Ser Ser Leu Gly
385                 390                 395                 400

Glu Trp Pro Trp Gln Val Ser Leu Gln Val Lys Leu Val Ser Gln Asn
                405                 410                 415

His Met Cys Gly Gly Ser Ile Ile Gly Arg Gln Trp Ile Leu Thr Ala
        420                 425                 430

Ala His Cys Phe Asp Gly Ile Pro Tyr Pro Asp Val Trp Arg Ile Tyr
        435                 440                 445

Gly Gly Ile Leu Asn Leu Ser Glu Ile Thr Asn Lys Thr Pro Phe Ser
        450                 455                 460

Ser Ile Lys Glu Leu Ile Ile His Gln Lys Tyr Lys Met Ser Glu Gly
465                 470                 475                 480

Ser Tyr Asp Ile Ala Leu Ile Lys Leu Gln Thr Pro Leu Asn Tyr Thr
                485                 490                 495

Glu Phe Gln Lys Pro Ile Cys Leu Pro Ser Lys Ala Asp Thr Asn Thr
        500                 505                 510

Ile Tyr Thr Asn Cys Trp Val Thr Gly Trp Gly Tyr Thr Lys Glu Arg
        515                 520                 525

Gly Glu Thr Gln Asn Ile Leu Gln Lys Ala Thr Ile Pro Leu Val Pro
        530                 535                 540

Asn Glu Glu Cys Gln Lys Lys Tyr Arg Asp Tyr Val Ile Thr Lys Gln
545                 550                 555                 560

Met Ile Cys Ala Gly Tyr Lys Glu Gly Gly Ile Asp Ala Cys Lys Gly
                565                 570                 575

Asp Ser Gly Gly Pro Leu Val Cys Lys His Ser Gly Arg Trp Gln Leu
        580                 585                 590

Val Gly Ile Thr Ser Trp Gly Glu Gly Cys Ala Arg Lys Glu Gln Pro
        595                 600                 605
```

-continued

Gly Val Tyr Thr Lys Val Ala Glu Tyr Ile Asp Trp Ile Leu Glu Lys
    610                 615                 620

Ile Gln Ser Ser Lys Glu Arg Ala Leu Glu Thr Ser Pro Ala
625                 630                 635

<210> SEQ ID NO 6
<211> LENGTH: 615
<212> TYPE: PRT
<213> ORGANISM: Homo sapiens

<400> SEQUENCE: 6

Met Arg Ala Leu Leu Leu Gly Phe Leu Leu Val Ser Leu Glu Ser
1               5                   10                  15

Thr Leu Ser Ile Pro Pro Trp Glu Ala Pro Lys Glu His Lys Tyr Lys
                20                  25                  30

Ala Glu Glu His Thr Val Val Leu Thr Val Thr Gly Glu Pro Cys His
            35                  40                  45

Phe Pro Phe Gln Tyr His Arg Gln Leu Tyr His Lys Cys Thr His Lys
        50                  55                  60

Gly Arg Pro Gly Pro Gln Pro Trp Cys Ala Thr Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
                325                 330                 335

Thr Pro Gly Ala Leu Pro Ala Lys Arg Glu Gln Pro Pro Ser Leu Thr
            340                 345                 350

-continued

Arg Asn Gly Pro Leu Ser Cys Gly Gln Arg Leu Arg Lys Ser Leu Ser
                355                 360                 365

Ser Met Thr Arg Val Val Gly Gly Leu Val Ala Leu Arg Gly Ala His
        370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
                405                 410                 415

Arg Pro Ala Pro Glu Asp Leu Thr Val Val Leu Gly Gln Glu Arg Arg
                420                 425                 430

Asn His Ser Cys Glu Pro Cys Gln Thr Leu Ala Val Arg Ser Tyr Arg
                435                 440                 445

Leu His Glu Ala Phe Ser Pro Val Ser Tyr Gln His Asp Leu Ala Leu
        450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
        500                 505                 510

Glu Glu Tyr Ala Ser Phe Leu Gln Glu Ala Gln Val Pro Phe Leu Ser
                515                 520                 525

Leu Glu Arg Cys Ser Ala Pro Asp Val His Gly Ser Ser Ile Leu Pro
                530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
                580                 585                 590

Arg Asn Lys Pro Gly Val Tyr Thr Asp Val Ala Tyr Tyr Leu Ala Trp
                595                 600                 605

Ile Arg Glu His Thr Val Ser
        610                 615

<210> SEQ ID NO 7
<211> LENGTH: 304
<212> TYPE: PRT
<213> ORGANISM: Artificial Sequence
<220> FEATURE:
<223> OTHER INFORMATION: Synthetic polypeptide

<400> SEQUENCE: 7

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
                20                  25                  30

Asp Glu Glu His Thr Ile Ile Thr Asp Thr Glu Leu Pro Pro Leu Lys
        35                  40                  45

Leu Met His Ser Phe Cys Ala Phe Lys Ala Asp Asp Gly Pro Cys Lys
        50                  55                  60

Ala Ile Met Lys Arg Phe Phe Phe Asn Ile Phe Thr Arg Gln Cys Glu
65              70                  75                  80

Glu Phe Ile Tyr Gly Gly Cys Glu Gly Asn Gln Asn Arg Phe Glu Ser
                85                  90                  95

```
Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
            115                 120                 125

Glu Asp Pro Gly Ile Cys Arg Gly Tyr Ile Thr Arg Tyr Phe Tyr Asn
            130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
            195                 200                 205

Phe Glu Phe His Gly Pro Ser Trp Cys Leu Thr Pro Ala Asp Arg Gly
            210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
            275                 280                 285

Lys Gln Arg Val Lys Ile Ala Tyr Glu Glu Ile Phe Val Lys Asn Met
            290                 295                 300

<210> SEQ ID NO 8
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 8

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
50                  55

<210> SEQ ID NO 9
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30

Ile Met Met Trp Val Arg Gln Ala Pro Gly Lys Gly Leu Glu Trp Val
```

```
                35                  40                  45
Ser Gly Ile Tyr Ser Ser Gly Gly Ile Thr Val Tyr Ala Asp Ser Val
 50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Tyr Arg Arg Ile Gly Val Pro Arg Arg Asp Glu Phe Asp Ile Trp
            100                 105                 110
Gly Gln Gly Thr Met Val Thr Val Ser Ser
            115                 120
```

```
<210> SEQ ID NO 10
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 10

Asp Ile Gln Met Thr Gln Ser Pro Ser Thr Leu Ser Ala Ser Val Gly
 1               5                  10                  15
Asp Arg Val Thr Ile Thr Cys Arg Ala Ser Gln Ser Ile Ser Ser Trp
                20                  25                  30
Leu Ala Trp Tyr Gln Gln Lys Pro Gly Lys Ala Pro Lys Leu Leu Ile
            35                  40                  45
Tyr Lys Ala Ser Thr Leu Glu Ser Gly Val Pro Ser Arg Phe Ser Gly
 50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Thr Tyr Trp Thr
                85                  90                  95
Phe Gly Gln Gly Thr Lys Val Glu Ile
            100                 105
```

```
<210> SEQ ID NO 11
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 11

Glu Ala Met His Ser Phe Cys Ala Phe Lys Ala Asp Asp Gly Pro Cys
 1               5                  10                  15
Arg Ala Ala His Pro Arg Trp Phe Phe Asn Ile Phe Thr Arg Gln Cys
                20                  25                  30
Glu Glu Phe Ile Tyr Gly Gly Cys Glu Gly Asn Gln Asn Arg Phe Glu
            35                  40                  45
Ser Leu Glu Glu Cys Lys Lys Met Cys Thr Arg Asp
 50                  55                  60
```

```
<210> SEQ ID NO 12
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 12
```

```
Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
                20              25                  30

Phe Ser Tyr Gly Gly Cys Gly Gly Asn Gln Asn Arg Phe Glu Ser Leu
            35              40                  45

Glu Glu Cys Lys Lys Met Cys Thr Arg Asp
        50              55
```

EVALUATION, ASSAYS AND TREATMENT OF PKAL-MEDIATED DISORDERS

CROSS-REFERENCE TO RELATED APPLICATIONS

This application is a divisional of U.S. application Ser. No. 14/761,671, filed Jul. 17, 2015, issued as U.S. Pat. No. 10,609,670, which is a national stage filing under 35 U.S.C. § 371 of international PCT application PCT/US2014/012090, filed on Jan. 17, 2014, which claims the benefit of U.S. Provisional Application No. 61/754,600, filed Jan. 20, 2013, each of which is incorporated by reference herein in its entirety.

BACKGROUND

Plasma kallikrein (pKal) is the primary bradykinin-generating enzyme in the circulation. The activation of pKal occurs via the contact system which has been linked to disease pathology associated with hereditary angioedema (HAE). Bradykinin is a key mediator of pain, inflammation, edema and angiogenesis.

Plasma protease C1 inhibitor (also known as C1-inhibitor or C1-INH) is a protease inhibitor belonging to the serpin superfamily. Its main function is the inhibition of the complement system to prevent spontaneous activation. Hereditary angioedema types I and II are caused by genetic deficiencies of C1-INH, which lead to overproduction of bradykinin.

SUMMARY OF THE INVENTION

The currently available functional diagnostic assays for investigating C1-INH employ inhibition of activated C1s and thus the complement system. The present disclosure is based on the development of new diagnostic assays that employ inhibition of PKal, FXII, or both, thus the PKal-mediated signaling pathway. Surprisingly, the diagnostic assays described herein successfully distinguished 100% of patients having HAE types I and II from control patients.

Accordingly, one aspect of the present disclosure features a method, comprising: (a) contacting a sample containing plasma protease C1 inhibitor (C1-INH) with a capture reagent, and (b) measuring a level of the C1-INH in the sample that binds to the capture reagent. The capture reagent comprises: i) an active form of Factor XII, or a C1-INH-binding fragment thereof, ii) an active form of plasma kallikrein, or a C1-INH-binding fragment thereof, or iii) a combination of i) and ii). For example, the capture reagent can be the active form of Factor XII, the active form of plasma kallikrein, or a combination thereof. Any of the capture reagents for use in the assays described herein can be immobilized on a substrate.

In some embodiments, the level of the C1-INH that binds to the capture agent is measured using a detection agent that binds C1-INH, for example, an antibody that binds C1-INH. In some embodiments, the level of C1-INH that binds to the capture agent is measured by an enzyme-linked immunosorbent assay (ELISA).

The sample containing C1-INH (e.g., a blood sample or a plasma sample) can be obtained from a subject. In some examples, the subject has a symptom of a pKal-mediated disorder, which can be edema, recurrent attacks of swelling; swelling wherein said swelling is completely or predominantly peripheral; hives; redness, pain, and swelling in the absence of evidence of infection; or non-histamine-mediated edema. In other examples, the subject is resistant to an anti-histamine therapy, a corticosteroid therapy, or both. In yet other examples, the subject has no symptom of a pKal-mediated disorder at the time the sample is collected, has no history of a symptom of a pKal-mediated disorder, or no history of a pKal-mediated disorder.

In some embodiments, the method described herein further comprises identifying the subject as being at risk for or having a pKal-mediated disorder if the level of C1-INH that binds the capture reagent in the sample is reduced as compared to a reference value. The pKal-mediated disorder can be histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema (HAE), pulmonary embolism, stroke, head trauma or peri-tumor brain edema, sepsis, acute middle cerebral artery (MCA) ischemic event (stroke), restenosis, systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases, or tissue injuries. In some examples, the pKal-mediated disorder is HAE.

If the subject is identified as being at risk for or having a pKal-mediated disorder (e.g., HAE), the method described herein can further comprise administering to the subject an effective amount of a therapeutic agent, wherein the therapeutic agent is selected from the group consisting of a kallikrein binding agent; a bradykinin B2 receptor antagonist, and a C1-INH replacement agent. In some instances, the therapeutic agent is DX-88, DX-2930, or EPIKAL-2.

Another aspect of the present disclosure features a method for treating a subject (e.g., a human patient) having a pKal-mediated disorder (e.g., HAE), the method comprising administering to the subject an effective amount of a therapeutic agent, which is a kallikrein binding agent, a bradykinin B2 receptor antagonist, or a C1-INH replacement agent. The subject to be treated by this method has a reduced level of C1-INH that is capable of binding to a capture reagent as compared to a reference value. The capture reagent comprises: i) an active form of Factor XII, or a C1-INH-binding fragment thereof; ii) an active form of kallikrein, or a C1-INH-binding fragment thereof, or iii) a combination of i) and ii). The C1-INH level of the subject can be determined by any of the assay methods described herein.

In some examples, the therapeutic agent is DX-88, DX-2930, or EPIKAL-2.

Also within the scope of the present disclosure are pharmaceutical compositions for use in treating a treating a subject (e.g., a human patient) having a pKal-mediated disorder (e.g., HAE) and a reduced level of C1-INH that is capable of binding to a capture reagent as compared to a reference value. The pharmaceutical composition comprises a therapeutic agent for treating the disorder, which can be a kallikrein binding agent, a bradykinin B2 receptor antagonist, or a C1-INH replacement agent, and a pharmaceutically acceptable carrier. The present disclosure also provides uses of the pharmaceutical compositions described herein in manufacturing medicaments for use in treating the PKal-mediated disorders such as HAE. In another aspect, the present disclosure provides a kit for detecting plasma protease C1 inhibitor (C1-INH) capable of binding to a capture reagent.

The kit can comprise: a) a capture reagent that comprises:
i) an active form of Factor XII, or a C1-INH-binding fragment thereof;
ii) an active form of kallikrein, or a C1-INH-binding fragment thereof; or
iii) a combination of i) and ii); and
b) a detection reagent that binds C1-INH, and optionally, c) C1-INH.

In some embodiments, the capture reagent, which can be FXIIa, the active form of PKal, or a combination thereof, is immobilized on a substrate. In some embodiments, the detection reagent is an anti-C1-INH antibody.

Further, the present disclosure provides a method for evaluating a treatment of a pKal-mediated disorder in a subject (e.g., a human HAE patient), comprising: (a) measuring the levels of plasma protease C1 inhibitor (C1-INH) that is capable of inhibiting plasma kallikrein, Factor XII, or both in samples collected from the subject before and after the treatment or during the course of the treatment, and (b) evaluating effectiveness of the treatment based on the levels of the C1-INH, wherein a decrease of the C1-INH level after the treatment or over the course of the treatment indicates that the treatment is effective on the subject.

In some embodiments, the treatment involves a kallikrein binding agent, a bradykinin B2 receptor angatonist, or a C1-INH replacement agent. For example, the treatment involves DX-88, DX-2930, or EPIKAL-2. Alternatively or in addition, the samples collected from the subject is blood samples or plasma samples.

In some embodiments, the levels of the C1-INH can be measured an assay method as described herein. For example, the levels of the C1-INH can be measured by a process comprising: (a) contacting the samples collected from the subject with a capture reagent (e.g., immobilized on a substrate), and (b) measuring a level of the C1-INH in the sample that binds to the capture reagent, which can comprise: i) an active form of Factor XII, or a C1-INH-binding fragment thereof, ii) an active form of plasma kallikrein, or a C1-INH-binding fragment thereof, or iii) a combination of i) and ii). In some examples, the capture reagent comprises the active form of Factor XII, the active form of plasma kallikrein, or a combination thereof. In any of the assays described herein, the levels of the C1-INH can be measured using a detection agent that binds C1-INH, e.g., an antibody that binds C1-INH. In some examples, the levels of the C1-INH is measured by an enzyme-linked immunosorbent assay (ELISA).

The following embodiments are also within the scope of the present disclosure.

The present disclosure provides methods of evaluating (e.g., identifying) a subject, e.g., a subject at risk for or suffering from (e.g., having) a pKal-mediated or bradykinin-mediated disorder. Provided methods permit analysis of patients with plasma kallikrein-mediated angioedema (KMA), or other diseases mediated by pKal useful in the evaluation and treatment.

Embodiments of the invention provide a biomarker and use thereof in the identification and treatment of patients, e.g., patients suffering from edema caused by bradykinin that is generated by plasma kallikrein. Methods, compositions and devices disclosed herein are useful in a number of ways. For example, levels of a pKal marker can be used to identify disorders associated with elevated contact system activation. Initial screening can be followed up with in vitro or in vivo testing with plasma kallikrein inhibitors (e.g. DX-88, EPI-KAL2, or DX-2930), e.g., in preclinical models of disease. A marker disclosed herein can also be used as a pharmacodynamic biomarker or to otherwise monitor the response of a subject to a kallikrein inhibitor. A marker disclosed herein can be used in a companion diagnostic to enable treatment of diseases mediated by plasma kallikrein, manage dosing during prophylactic therapy of a pKal-mediated or bradykinin-mediated disorder, e.g., HAE, non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, thrombosis associated with ventricular assist devices, heparin-induced thrombocytopenia with thrombosis, thromboembolic disease, and coronary heart disease with unstable angina pectoris.

In one aspect, the present invention provides a method of evaluating a subject, e.g., a subject at risk for a pKal-mediated disorder, a bradykinin-mediated disorder, e.g., anti-histamine resistant edema or HAE, comprising: a) acquiring a sample comprising subject tissue, e.g., blood, plasma, or tears; b) contacting said sample, e.g., in vitro, with one or more capture reagent under conditions sufficient for the formation of a complex between C1-INH and said one or more capture reagent, wherein said capture reagent comprises one or both of: i) a moiety comprising an active form of Factor XII, or a C1-INH-binding fragment thereof; or ii) a moiety comprising an active form of kallikrein, or a C1-INH-binding fragment thereof; and c) evaluating the level of binding of CI-INH to said capture reagent.

In some embodiments, said evaluating comprises comparing the determined the level of binding of CI-INH to said capture reagent with a reference, wherein a level that meets a predetermined criterion, e.g., if it is at or below a reference, is indicative of a disorder susceptible to treatment with a pKal inhibitor. The reference can be, e.g., the level in a person not having a pKal-mediated disorder, e.g., a person not having HAE, or other disorder described herein, or having no history of a symptom of such a disorder.

In some embodiments, the pKal-mediated disorder is selected from: HAE, non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

In some embodiments, said subject is evaluated for susceptibility to pKal-mediated disorder. In certain embodiments, said subject has a symptom of, e.g., consistent with, a pKal-mediated disorder, e.g., edema. In certain embodiments, said subject has a symptom of a disorder characterized by unwanted pKal activation and said subject has been administered an anti-histamine therapy, or corticosteroid therapy and the symptoms were resistant thereto. In some embodiments, said subject has one or more or all of the following symptoms or properties: recurrent attacks of swelling; swelling wherein said swelling is completely or predominantly peripheral, e.g., the subject has no significant abdominal or airway swelling; hives; redness, pain, and swelling in the absence of evidence of infection; fails to respond to antihistamine or corticosteroid therapy; or has non-histamine-mediated edema.

In some embodiments, said subject has persistent or recurring edema and is non-responsive to one or both of anti-histamine and steroid therapy.

In some embodiments, the subject the subject has a no history of a pKal-mediated disorder, e.g., HAE, IAE, IBD, or IBS. In some embodiments, the subject has a history of a pKal-mediated disorder, e.g., HAE, IAE, IBD, or IBS. In some embodiments, the subject has no history of HAE. In some embodiments, the subject has a history of HAE. In some embodiments, the subject has no history of IAE. In some embodiments, the subject has a history of IAE. In some embodiments, the subject has no history of IBD or IBS. In some embodiments, the subject has a history of IBD or IBS. In some embodiments, the subject has a no history of a histamine mediated disorder, e.g., a food allergy. In some embodiments, the subject has a history of a histamine mediated disorder, e.g., a food allergy. In some embodiments, the subject has a no history of a pKal-mediated disorder, e.g., HAE, IAE, IBD, or IBS, and has no history of a histidine-mediated disorder, e.g., a food allergy. In some embodiments, the subject has no history of a pKal-mediated disorder, e.g., HAE, IAE, IBD, or IBS, and has a history of a histamine-mediated disorder, e.g., a food allergy. In some embodiments, the subject has a history of a pKal-mediated disorder, e.g., HAE, IAE, IBD, or IBS, and has no history of a histidine-mediated disorder, a food allergy. In some embodiments, the subject has a history of a pKal-mediated disorder, e.g., HAE, IAE, IBD, or IBS, and has a history of a histamine-mediated disorder, e.g., a food allergy.

In certain embodiments, said subject has a history of angioedema. In certain embodiments, said subject has no history of angioedema. In particular embodiments, said subject is not suffering from a symptom characteristic of a pKal or bradykinin mediated disorder, e.g., edema. In certain embodiments, said subject undergoing an angioedema attack when said tissue was removed from the subject's body.

In some embodiments, said one or more capture reagent is disposed on a substrate. In certain embodiments, the substrate is an insoluble substrate. In some embodiments, said one or more capture reagent comprises an active form of Factor XII, or a C1-INH-binding fragment thereof. In particular embodiments, said one or more capture reagent comprises an active form of kallikrein, or a C1-INH-binding fragment thereof. In particular embodiments, said one or more capture reagent comprises an active form of Factor XII, or a C1-INH-binding fragment thereof and an active form of kallikrein, or a C1-INH-binding fragment thereof.

In some embodiments, said method does not include evaluating the binding of C1-INH to activated C1, e.g., C1s.

In some embodiments, said one or more capture reagent comprises a first specific binding moiety which forms a complex with a second specific binding moiety disposed on said substrate. In certain embodiments, said first and second binding moiety are selected from biotin and avidin.

In some embodiments, said method comprises, e.g., in said evaluation, evaluating the binding of a detection reagent with said complex, e.g., a detection reagent that binds complexed C1INH, e.g., an anti-C1NH antibody, e.g., the detection reagent can bind C1INH prior to or after formation of a complex between the C1IHN and the capture reagent. In certain embodiments, the method comprises supplying a detection reagent under conditions sufficient to form a complex between C1-INH and a detection reagent. In some embodiments, said C1-INH is complexed with capture reagent. In particular embodiments, said method comprises forming a complex comprising a detection reagent, C1-INH, and capture reagent, wherein said detection reagent is complexed with said C1-INH, said CI-INH is complexed with capture reagent.

In some embodiments, the capture reagent comprises a moiety comprising an active form of Factor XII, or a C1-INH-binding fragment thereof. In some embodiments, the capture reagent comprises a moiety comprising an active form of kallikrein, or a C1-INH-binding fragment thereof. In some embodiments, the capture reagent comprises one or both of: i) a moiety comprising an active form of Factor XII, or a C1-INH-binding fragment thereof, or ii) a moiety comprising an active form of kallikrein, or a C1-INH-binding fragment thereof. In particular embodiments, the capture reagent comprises a moiety comprising an active form of Factor XII, or a C1-INH-binding fragment thereof. In particular embodiments, the capture reagent comprises a moiety comprising an active form of kallikrein, or a C1-INH-binding fragment thereof. In particular embodiments, the capture reagent comprises both a moiety comprising an active form of Factor XII, or a C1-INH-binding fragment thereof and a moiety comprising an active form of Factor XII, or a C1-INH-binding fragment thereof.

In some embodiments, the capture reagent further comprises a moiety which binds said complex to a substrate. In certain embodiments, said moiety comprises a first and a second binding partner, wherein one is bound to said capture reagent and the other is bound to said substrate.

In some embodiments, the method further comprises administering a therapeutic agent disclosed herein to said subject. In certain embodiments, said therapeutic agent is selected from: a kallikrein binding agent; a bradykinin B2 receptor antagonist; or a C1-INH replacement agent. In particular embodiments, said therapeutic agent comprises DX-88. In particular embodiments, said therapeutic agent comprises DX-2930. In particular embodiments, said therapeutic agent comprises EPIKAL-2. In some embodiments, the method further comprises administering a second therapy.

In some embodiments, the method comprises determining if said subject has HAE.

In another aspect, the present invention provides a method of evaluating a subject for HAE type, comprising: (i) acquiring a value for C1-INH function for the subject by methods disclosed herein (e.g., measuring a level of the C1-INH in the sample that binds to the capture reagent); and (ii) acquiring a value for total C1-INH protein level (e.g., measuring a total C1-INH level); wherein if the value for C1-INH function provided by (i) meets a preselected criterion, e.g., it is below a reference value, and the value for C1-INH protein level provided by (ii) meets a preselected criterion, e.g., it is above a reference value, then categorizing the subject as having type II HAE. In some embodiments, at least one of (i) and (ii) is directly acquired.

In another aspect, the present invention provides a method of treating a subject comprising, acquiring an evaluation of said subject made by methods disclosed herein; and responsive thereto, selecting a therapy for, or administering a therapy to, said patient. In some embodiments, the method further comprises administering a therapeutic agent disclosed herein to said subject. In certain embodiments, said therapeutic agent is selected from: a kallikrein binding agent; a bradykinin B2 receptor antagonist; or a C1-INH replacement agent. In particular embodiments, said therapeutic agent comprises DX-88. In particular embodiments, said therapeutic agent comprises DX-2930. In particular embodiments, said therapeutic agent comprises EPIKAL-2.

In another aspect, the present invention provides a method of treating a subject comprising: providing a subject that has been evaluated by methods disclosed herein; and responsive thereto, selecting a therapy for, or administering a therapy to, said patient. In some embodiments, the method further comprises administering a therapeutic agent disclosed herein to said subject. In certain embodiments, said therapeutic agent is selected from: a kallikrein binding agent; a bradykinin B2 receptor antagonist; or a C1-INH replacement agent. In particular embodiments, said therapeutic agent comprises DX-88. In particular embodiments, said therapeutic agent comprises DX-2930. In particular embodiments, said therapeutic agent comprises EPIKAL-2.

In a further aspect, the present invention provides a reaction mixture comprising a capture reagent described herein, optionally, complexed with C1-IHN, and optionally complexed with a detection reagent. In embodiments the reaction mixture comprises subject plasma. In some embodiments uncomplexed elements of the sample have been removed, e.g., by washing.

In a further aspect, the present invention provides a substrate comprising one or more capture agents as described herein, e.g., one or both of i) a moiety comprising an active form of Factor XII, or a C1-INH-binding fragment thereof; or ii) a moiety comprising an active form of kallikrein, or a C1-INH-binding fragment thereof. In some embodiments, said substrate comprises moiety i and ii, disposed in individually addressable regions.

In yet another aspect, the present invention provides a device comprising a substrate, on which is disposed, at least one and in embodiment both capture reagents disclosed herein. In embodiments a first capture reagent is disposed at a first region and the second capture reagent is disposed at a second region of said substrate, e.g., in different wells.

In another aspect, the present invention provides a kit comprising one or more of: one or both capture reagents described herein, optionally disposed on a substrate; a detection reagent, e.g., an antiC1-INH antibody or an anti-anti-C1-INH antibody; and standards, e.g., C1-INH.

The details of one or more embodiments of the invention are set forth in the accompanying drawings and the description below. Other features, objects, and advantages of the invention will be apparent from the description and drawings, and from the claims.

The contents of all cited references including literature references, issued patents, published or non-published patent applications cited throughout this application as well as those listed below are hereby expressly incorporated by reference in their entireties for the purposes or subject matter referenced herein.

BRIEF DESCRIPTION OF DRAWINGS

FIG. 4A depicts data from a commercially available functional ELISA for measuring C1-INH based on inhibition of C1s. FIG. 4B depicts data from an exemplary functional ELISA assay for measuring C1-INH based on inhibition of kallikrein. FIG. 4C depicts data from an exemplary functional ELISA assay for measuring C1-INH based on inhibition of FXII.

DETAILED DESCRIPTION

Figure 1:
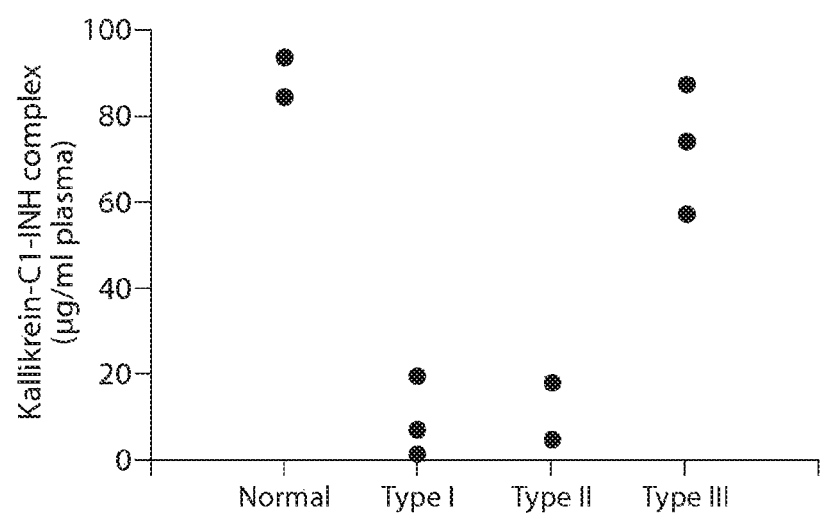
FIG. 1 depicts exemplary detection of Kallikrein-C1-INH complex formation by ELISA. From left to right—normal control, Type I HAE, Type II HAE and Type III HAE patient plasma samples.

Plasma kallikrein (PKal) is a serine protease component of the contact system and is the primary bradykinin-generating enzyme in the circulation. The contact system is activated by either factor XIIa (the active form of Factor XII or FXII) upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH) leads to hereditary angioedema (HAE). Patients with HAE suffer from acute attacks of painful edema often precipitated by unknown triggers (Zuraw B. L. et al., N Engl J Med 359, 1027-1036, 2008). Through the use of pharmacological agents or genetic studies in animal models, the plasma kallikrein-kinin system (plasma KKS) has been implicated in various diseases.

Hereditary angioedema (HAE), types I and II, is an autosomal dominant disorder characterized by swelling in the extremities, face, gastrointestinal tract or upper airways (1). Attacks last 2-5 days and if not treated appropriately, swelling of the larynx, in particular, can be fatal. Since this is a rare disorder (affects 1:20,000 to 1:50,000 people) with a variable presentation, the diagnosis may be missed. HAE is typically caused by a heterozygous mutation in the C1-INH gene which results in either reduced protein levels (type I HAE, 85% of cases) or reduced function (type II HAE, 15%) (2). In type I HAE, C1-INH protein level is low and the functional level is proportionately low, whereas in type II HAE, the protein level is normal, or even elevated, but the functional level is low. Thus a functional assay is requisite, not only to confirm the diagnosis of HAE, but also type II disease cannot be diagnosed without it.

C1 INH is a serine protease enzyme that inhibits activated proteins of the complement, coagulation, and kinin forming cascades. The currently available assays used to assess C1-INH functional level measure the inhibition of C1s of the complement cascade by C1-INH, utilizing either a chromogenic assay or a complex ELISA method. The chromogenic assay is generally considered preferable (3) but both methods have limitations. The chromogenic assay is more likely to have an occasional false positive while the complex ELISA has a negative predictive value of only 62%.

A limitation of both the complex ELISA and chromogenic methods known in the art is that the assays measure the activity of C1-INH on an enzyme of the complement cascade, which is not the cause of PKal-mediated diseases such as HAE. Indeed, a dysfunctional C1-INH has been reported to have normal activity on the kinin-forming cascade, hence no angioedema occurs, but it fails to inhibit C1s so that C1 is abnormally active and C4 is depleted (7). Thus, the currently available technology would not allow for measuring the level of C1-INH that is functional in inhibiting the kinin-forming cascade (e.g., inhibiting PKal and/or FXIIa).

The present disclosure is based on the development of novel assays for measuring functional C1-INH employing ELISA methodology based on either inhibition of activated factor XII, or plasma kallikrein, for the diagnosis of HAE types I & II. These assays have physiologic relevance particularly with diseases/disorders associated with the PKal signaling pathway and therefore would be a major advance over the methods known in the art.

Described herein are new assay methods for measuring the levels of C1-INH based on the inhibition of PKal and/or FXII (e.g., active forms of the proteins) and kits for carrying out the assay methods. Also described herein are the application of such assay methods in diagnosing patients having or at risk for a disease/disorder mediated by PKal such as HAE or evaluating a treatment of the disease/disorder.

Definitions

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

As used herein, the term "acquire" or "acquiring" refers to obtaining possession of a physical entity, or a value, e.g., a numerical value, by "directly acquiring" or "indirectly acquiring" the physical entity or the value. "Directly acquiring" means performing a process (e.g., performing an assay or test on a sample or "analyzing a sample" as that term is defined herein) to obtain the physical entity or value. "Indirectly acquiring" refers to receiving the physical entity or value from another party or source (e.g., a third party laboratory that directly acquired the physical entity or value). Directly acquiring a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, "analyzing" a sample includes performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Analyzing a sample can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

The term "agonist," as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound which increases at least one bioactivity of a protein. An agonist can also be a compound which increases the interaction of a polypeptide with another molecule, e.g., a target peptide or nucleic acid.

The term "antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound which reduces or inhibits the amount of expressed protein present. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ $M^{-1}$ for a particular target molecule. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM $CaCl_2$) at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound] = N \cdot [Free]/((1/Ka) + [Free]).$$

It is not always necessary to make an exact determination of $K_g$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding protein" refers to a protein that can interact with a target molecule. This term is used interchangeably with "ligand." A "plasma kallikrein binding protein" refers to a protein that can interact with (e.g., bind) plasma kallikrein, and includes, in particular, proteins that preferentially or specifically interact with and/or inhibit plasma kallikrein. A protein inhibits plasma kallikrein if it causes a decrease in the activity of plasma kallikrein as compared to the activity of plasma kallikrein in the absence of the protein and under the same conditions. In some embodiments, the plasma kallikrein binding protein is an antibody.

The term "capture reagent" refers to a moiety that binds specifically to its ligand.

As used herein, the terms "complex" or "complex formation" refer to a complex between members having a specific affinity for one another.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

As used herein, a "detection reagent" refers to a moiety that binds to the moiety to be detected. Typically it generates a signal, e.g., fluorescence, or produces of a measurable compound.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding protein (e.g., antibody) "binds to the same epitope" as a second binding protein (e.g., antibody) if the first binding protein binds to the same site on a target compound that the second binding protein binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding protein binds.

A first binding protein (e.g., antibody) "competes for binding" with a second binding protein (e.g., antibody) if the binding of the first binding protein to its epitope decreases (e.g., by 10%, 20%, 30%, 40%, 50%, 60%, 70%, 80%, 90%, 100%, or more) the amount of the second binding protein that binds to its epitope. The competition can be direct (e.g., the first binding protein binds to an epitope that is the same as, or overlaps with, the epitope bound by the second binding protein), or indirect (e.g., the binding of the first binding protein to its epitope causes a steric change in the target compound that decreases the ability of the second binding protein to bind to its epitope).

As used herein, a "functional" biological molecule is a biological molecule in a form in which it exhibits a property and/or activity by which it is characterized.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interest is at least 5, 10, 25, 50, 75, 80, 90, 92, 95, 98, or 99% pure on a weight-weight basis.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a human or non-human animal.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "isolated" protein refers to a protein that is removed from at least 90% of at least one component of a natural sample from which the isolated protein can be obtained. Proteins can be "of at least" a certain degree of purity if the species or population of species of interest is at least 5, 10, 25, 50, 75, 80, 90, 92, 95, 98, or 99% pure on a weight-weight basis.

The term "kallikrein" (e.g., plasma kallikrein) refers to peptidases (enzymes that cleave peptide bonds in proteins), a subgroup of the serine protease family. Plasma kallikrein cleaves kininogen to generate kinins, potent pro-inflammatory peptides.

The term "kallikrein inhibitor" refers to any agent or molecule that inhibits kallikrein. For example, DX-88 (also referred to herein as "PEP-1") is a potent (Ki<1 nM) and specific inhibitor of plasma kallikrein (NP_000883). (See also, e.g., WO 95/21601 or WO 2003/103475).

As used herein the term "DX-2922" as used interchangeably with the term "X101-A01". Other variants of this antibody are described below.

| Antibody Identification | Description |
| --- | --- |
| X63-G06 | Non-germlined Fab discovered using ROLIC, same HC but different LC as M160-G12 |
| X81-B01 | Germlined IgG produced in HEK 293T cells |
| X101-A01 | Germlined IgG produced in CHO cells, same HC and LC sequence as X81-B01 |
| DX-2922 | Alternate nomenclature for X101-A01 |

As used herein the term "DX-2930" as used interchangeably with the term "X124-G01". Other variants of this antibody are described below.

| Antibody Identification | Description |
| --- | --- |
| M162-A04 | Non-germlined Fab discovered using phage display |
| M199-A08 | Heavy chain CDR3 varied Fab derived by affinity maturation of M162-A04 |
| X115-F02 | Germlined Fab produced in 293T cells, same variable heavy chain as X124-G01 |
| X124-G01 or DX-2930 | Germlined IgG produced in CHO cells, LC and HC sequence as X115-F02 except that the C-terminal Lys of the HC is removed in X124-G01 (also known as DX-2930). |

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

A "patient," "subject" or "host" (these terms are used interchangeably) to be treated by the subject method may mean either a human or non-human animal. In some embodiments, a subject is suspected of or is at risk for or suffers from a kallikrein-mediated disorder, e.g., a bradykinin-mediated disorder, e.g., hereditary angioedema (HAE), non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

The terms "prekallikrein" and "preplasma kallikrein" are used interchangeably herein and refer to the zymogen form of active plasma kallikrein, which is also known as prekallikrein.

The term "preventing" or to "prevent" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

As used herein, a "sample" refers to a composition that comprises tissue, e.g., blood, plasma or protein, from a subject. A sample includes both an initial unprocessed sample taken from a subject as well as subsequently processed, e.g., partially purified or preserved forms. Exemplary samples include blood, plasma, tears, or mucus. In some embodiments, the sample is blood or plasma.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

"Treating" a disease (or condition) in a subject or "treating" a subject having a disease refers to subjecting the subject to a pharmaceutical treatment, e.g., the administration of a drug, such that at least one symptom of the disease is cured, alleviated or decreased.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Headings, including alphabetical or numerical headings, are merely for ease of understanding and reading and, absent express indication to the contrary, do not impose temporal order or a hierarchy of preferences.

Assay Methods and Kits for Measuring C1-INH based on Inhibition of PKal and/or FXII Provided herein are methods and kits for measuring the level of functional C1-INH based on the ability of C1-INH to bind to and inhibit active kallikrein and/or active FXII. Such a method may be carried out by contacting a sample containing C1-INH with a capture reagent as described herein, and measuring the level of the C1-INH in the same that binds the capture reagent. In some embodiments, the level of total C1-INH (e.g., the level of C1-INH protein in a sample, independent of whether the C1-INH binds to a capture reagent as described herein) is also measured.

Plasma protease C1 inhibitor (C1-INH) generally plays an important role in regulating various physiological pathways, including complement activation (e.g., inhibition of C1r and C1s proteases in the C1 complex), blood coagulation, fibrinolysis, and generation of kinins. C1-INH binds to and inhibits Factor XIIa, Factor XIIf, and kallikrein. C1-INH is a member of the serpin superfamily of proteins and has a 2 domain structure. The C-terminal serpin domain of C1-INH provides the protein's inhibitory activity. An exemplary amino acid sequence of human C1-INH is shown below (Accession No. NP_000053.2)

```
>gi|73858568|ref|NP_000053.2| plasma protease C1
inhibitor precursor [Homo sapiens]
                                    (SEQ ID NO: 1)
MASRLTLLTLLLLLLAGDRASSNPNATSSSSQDPESLQDRGEGKVATTVI

SKMLFVEPILEVSSLPTTNSTTNSATKITANTTDEPTTQPTTEPTTQPTI

QPTQPTTQLPTDSPTQPTTGSFCPGPVTLCSDLESHSTEAVLGDALVDFS

LKLYHAFSAMKKVETNMAFSPFSIASLLTQVLLGAGENTKTNLESILSYP

KDFTCVHQALKGFTTKGVTSVSQIFHSPDLAIRDTFVNASRTLYSSSPRV

LSNNSDANLELINTWVAKNTNNKISRLLDSLPSDTRLVLLNAIYLSAKWK

TTFDPKKTRMEPFHFKNSVIKVPMMNSKKYPVAHFIDQTLKAKVGQLQLS

HNLSLVILVPQNLKHRLEDMEQALSPSVFKAIMEKLEMSKFQPTLLTLPR

IKVTTSQDMLSIMEKLEFFDFSYDLNLCGLTEDPDLQVSAMQHQTVLELT

ETGVEAAAASAISVARTLLVFEVQQPFLFVLWDQQHKFPVFMGRVYDPRA
```

Active" or "functional" C1-INH refers to a C1-INH polypeptide or C1-INH polypeptide fragment that retains a biological and/or immunological activity similar, but not necessarily identical to naturally occurring C1-INH, including mature forms. In some embodiments, an active or functional C1-INH is a C1-INH polypeptide or C1-INH polypeptide fragment that binds to one or more of Factor XIIa, Factor XIIf, or kallikrein and inhibit the activity of FXIIa and/or PKal, thereby regulating the kinin-forming process.

In some embodiments, the sample being examined in the assay method described herein is a biological sample, e.g., a biological sample obtained from a subject as described herein, e.g., a body fluid sample such as a blood sample or a plasma sample. For example, a C1-INH protein suitable can be provided in biological tissue samples (e.g., blood, plasma, tears, mucus), tissue extracts or preparations, or solid tissues acquired directly from multi-cellular organisms (e.g., ex vivo procedures). Thus, among other things, the assays according to the invention can be used to monitor and/or characterize the endogenous C1-INH in human and other multicellular organisms for diagnosis or biomarker measurement.

A. Assay Format

The assay methods described herein permit evaluation (e.g., measurement) of the level CI-INH that binds to a capture reagent as described herein. The level (e.g., the amount) of C1-INH that binds to the capture reagent can be measured using assays described herein and/or assays known in the art. Assays that can be used for assessing levels of C1-INH that bind to the capture reagent include, but not limited to, immunoassays such as Western blots, enzyme linked immunosorbent assays (ELISAs) (e.g., sandwich ELISAs), radioimmunoassays, electrochemiluminescence-based detection assays, and related techniques. Methods for performing these exemplary assays are known in the art and commercially available (see, e.g., Current Protocols in Molecular Biology, Current edition, Wiley Online Library).

In some embodiments, the level of C1-INH that binds to the capture reagent is determined using an ELISA. ELISAs are known in the art (see, e.g., Crowther, John R (2009). "The ELISA Guidebook." $2^{nd}$ ed. Humana Press and Lequin R (2005). "Enzyme immunoassay (EIA)/enzyme-linked immunosorbent assay (ELISA)". Clin. Chem. 51 (12): 2415-8) and exemplary ELISAs are described herein. Kits for performing ELISAs are also known in the art and commercially available (see, e.g, ELISA kits from Life Technologies and BD Biosciences).

In some embodiments, provided assays are carried out on low-throughput platforms, including single assay format. For example, a low throughput platform may be used to measure the C1-INH activity level in biological samples (e.g., biological tissues, tissue extracts) for diagnosis or biomarker measurement.

In some embodiments, provided assays can be carried out on high throughput platforms. In some embodiments, multi-well plates, e.g., 24-, 48-, 96-, 384- or greater well plates, may be used for high throughput assays. Individual assays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform. For example, a commercially available plate reader (e.g., the plate::vision system available from Perkin Elmer, Waltham, MA) may be used. This plate reader is capable of kinetic-based fluorescence analysis. The plate::vision system has high collection efficiency optics and has special optics designed for the analysis of 96 wells in parallel. Additional suitable parallel plate readers include but are not limited to the SAFIRE® (Tecan, San Jose, CA), the FLIPRTETRA® (Molecular Devices, Union City, CA), the FDSS7000 (Hamamatsu, Bridgewater, NJ), and the CELLLUX® (Perkin Elmer, Waltham, MA).

In some embodiments, high throughput screening assays of the invention are automated (e.g., adapted to robotic assays).

B. Capture Reagents

The capture reagents for use in the assay methods described herein are capable of forming a complex with C1-INH that is functional in inhibiting the kinin-forming cascade, for example, inhibiting PKal, FXII, or both. In some embodiments, the capture reagent can comprise one or both of a moiety comprising an active form of Factor XII, or a C1-INH-binding fragment thereof; or a moiety comprising an active form of kallikrein, or a C1-INH-binding fragment thereof. In some embodiments, provided capture reagents are isolated and/or purified from a natural source. In some embodiments, provided capture reagents are recombinantly or synthetically produced. In some embodiments, a capture reagent is disposed on (e.g., bound to) a substrate, e.g., an insoluble substrate. The capture reagent may be bound to the substrate covalently or non-covalently. The capture reagent may be bound directly to the substrate, or may be bound indirectly, e.g., through a linker. Examples of linkers, include, but are not limited to, carbon-containing chains, polyethylene glycol (PEG), nucleic acids, monosaccharide units, biotin-avidin and peptides. In some embodiments, the substrate a container that comprises one or more wells, e.g., a microtiter plate. C1-INH-binding fragments of an active form of Factor XII or kallikrein can be made by generating fragments of the full length capture reagent and determining if the fragments bind to C1-INH.

In some embodiments, a capture reagent comprises a first specific binding moiety, e.g., biotin or avidin, which forms a complex with a second specific binding moiety, e.g., biotin or avidin, disposed on (e.g., bound to) a substrate, e.g., an insoluble substrate.

In some embodiments, the capture reagent can comprise a plasma kallikrein or a functional fragment thereof, a FXII or a functional fragment thereof, or a combination thereof.

(i) Plasma Kallikrein

Plasma kallikrein is a serine protease component of the contact system (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature.

Exemplary plasma kallikrein sequences can include human, mouse, or rat plasma kallikrein amino acid sequences, a sequence that is 80%, 85%, 90%, 95%, 96%, 97%, 98%, or 99% identical to one of these sequences, or a fragment thereof, e.g., of a sequence provided below. In some embodiments, plasma kallikrein is isolated from nature. In some embodiments, plasma kallikrein is produced by recombinant or synthetic means.

An exemplary sequence of human plasma kallikrein is shown below (accession number NP_000883.2). Human plasma kallikrein (86 kDa) was purified from human plasma and activated with factor XIIa. Factor XIIa activates prekallikrein by cleaving the polypeptide sequence at a single site (between Arg371-Ile372, cleavage site marked by "/" in the sequence below) to generate active plasma kallikrein, which then consists of two disulfide linked polypeptides; a heavy chain of approximately 52 kDa and a catalytic domain of approximately 34 kDa [Colman and Schmaier, (1997) "Contact System: A Vascular Biology Modulator With Anticoagulant, Profibrinolytic, Antiadhesive, and Proinflammatory Attributes" Blood, 90, 3819-3843].

```
                                         (SEQ ID NO: 2)
GCLTQLYENAFFRGGDVASMYTPNAQYCQMRCTFHPRCLLFSFLPASSIN

DMEKRFGCFLKDSVTGTLPKVHRTGAVSGHSLKQCGHQISACHRDIYKGV

DMRGVNFNVSKVSSVEECQKRCTSNIRCQFFSYATQTFHKAEYRNNCLLK

YSPGGTPTAIKVLSNVESGFSLKPCALSEIGCHMNIFQHLAFSDVDVARV

LTPDAFVCRTICTYHPNCLFFTFYTNVWKIESQRNVCLLKTSESGTPSSS

TPQENTISGYSLLTCKRTLPEPCHSKIYPGVDFGGEELNVTFVKGVNVCQ

ETCTKMIRCQFFTYSLLPEDCKEEKCKCFLRLSMDGSPTRIAYGTQGSSG

YSLRLCNTGDNSVCTTKTSTR/IVGGTNSSWGEWPWQVSLQVKLTAQRHL

CGGSLIGHQWVLTAAHCFDGLPLQDVWRIYSGILNLSDITKDTPFSQIKE
```

-continued
```
IIIHQNYKVSEGNHDIALIKLQAPLNYTEFQKPICLPSKGDTSTIYTNCW

VTGWGFSKEKGEIQNILQKVNIPLVTNEECQKRYQDYKITQRMVCAGYKE

GGKDACKGDSGGPLVCKHNGMWRLVGITSWGEGCARREQPGVYTKVAEYM

DWILEKTQSSDGKAQMQSPA
```

The human, mouse, and rat prekallikrein amino acid sequences, and the mRNA sequences encoding the same, are illustrated below. The sequences of prekallikrein are the same as plasma kallikrein, except that active plasma kallikrein (pKal) has the single polypeptide chain cleaved at a single position (indicated by the "/") to generate two chains. The sequences provided below are full sequences that include signal sequences. On secretion from the expressing cell, it is expected that the signal sequences are removed.

Human plasma kallikrein (ACCESSION: NP_000883.2)

```
>gi|78191798|ref|NP_000883.2| plasma kallikrein B1
precursor [Homo sapiens]
                                         (SEQ ID NO: 3)
MILFKQATYFISLFATVSCGCLTQLYENAFFRGGDVASMYTPNAQYCQMR

CTFHPRCLLFSFLPASSINDMEKREGCFLKDSVTGTLPKVHRTGAVSGHS

LKQCGHQISACHRDIYKGVDMRGVNENVSKVSSVEECQKRCTSNIRCQFF

SYATQTFHKAEYRNNCLLKYSPGGTPTAIKVLSNVESGESLKPCALSEIG

CHMNIFQHLAFSDVDVARVLTPDAFVCRTICTYHPNCLFFTFYTNVWKIE

SQRNVCLLKTSESGTPSSSTPQENTISGYSLLTCKRTLPEPCHSKIYPGV

DEGGEELNVTFVKGVNVCQETCTKMIRCQFFTYSLLPEDCKEEKCKCFLR

LSMDGSPTRIAYGTQGSSGYSLRLCNTGDNSVCTTKTSTR/IVGGTNSSW

GEWPWQVSLQVKLTAQRHLCGGSLIGHQWVLTAAHCFDGLPLQDVWRIYS

GILNLSDITKDTPFSQIKEIIIHQNYKVSEGNHDIALIKLQAPLNYTEFQ

KPICLPSKGDTSTIYTNCWVTGWGESKEKGEIQNILQKVNIPLVTNEECQ

KRYQDYKITQRMVCAGYKEGGKDACKGDSGGPLVCKHNGMWRLVGITSWG

EGCARREQPGVYTKVAEYMDWILEKTQSSDGKAQMQSPA
```

Mouse plasma kallikrein (ACCESSION: NP_032481.1)

```
>gi|6680584|ref|NP_032481.1| kallikrein B, plasma
1 [Mus musculus]
                                         (SEQ ID NO: 4)
MILFNRVGYFVSLFATVSCGCMTQLYKNTFFRGGDLAAIYTPDAQYCQKM

CTFHPRCLLFSFLAVTPPKETNKRFGCFMKESITGTLPRIHRTGAISGHS

LKQCGHQISACHRDIYKGLDMRGSNFNISKTDNIEECQKLCTNNFHCQFF

TYATSAFYRPEYRKKCLLKHSASGTPTSIKSADNLVSGFSLKSCALSEIG

CPMDIFQHSAFADLNVSQVITPDAFVCRTICTFHPNCLFFTFYTNEWETE

SQRNVCFLKTSKSGRPSPPIPQENAISGYSLLTCRKTRPEPCHSKIYSGV

DFEGEELNVTFVQGADVCQETCTKTIRCQFFIYSLLPQDCKEEGCKCSLR

LSTDGSPTRITYGMQGSSGYSLRLCKLVDSPDCTTKINAR/IVGGTNASL

GEWPWQVSLQVKLVSQTHLCGGSIIGRQWVLTAAHCFDGIPYPDVWRIYG

GILSLSEITKETPSSRIKELIIHQEYKVSEGNYDIALIKLQTPLNYTEFQ

KPICLPSKADTNTIYTNCWVTGWGYTKEQGETQNILQKATIPLVPNEECQ
```

KKYRDYVINKQMICAGYKEGGTDACKGDSGGPLVCKHSGRWQLVGITSWG

EGCGRKDQPGVYTKVSEYMDWILEKTQSSDVRALETSSA

Rat plasma kallikrein (ACCESSION: NP_036857.2)

```
>gi|162138905|ref|NP_036857.2| kallikrein B,
plasma 1 [Rattus norvegicus]
                                          (SEQ ID NO: 5)
```
MILFKQVGYFVSLFATVSCGCLSQLYANTFFRGGDLAAIYTPDAQHCQKM

CTFHPRCLLFSFLAVSPTKETDKRFGCFMKESITGTLPRIHRTGAISGHS

LKQCGHQLSACHQDIYEGLDMRGSNFNISKTDSIEECQKLCTNNIHCQFF

TYATKAFHRPEYRKSCLLKRSSSGTPTSIKPVDNLVSGFSLKSCALSEIG

CPMDIFQHFAFADLNVSHVVTPDAFVCRTVCTFHPNCLFFTFYTNEWETE

SQRNVCFLKTSKSGRPSPPIIQENAVSGYSLFTCRKARPEPCHFKIYSGV

AFEGEELNATFVQGADACQETCTKTIRCQFFTYSLLPQDCKAEGCKCSLR

LSTDGSPTRITYEAQGSSGYSLRLCKVVESSDCTTKINAR/IVGGTNSSL

GEWPWQVSLQVKLVSQNHMCGGSIIGRQWILTAAHCFDGIPYPDVWRIYG

GILNLSEITNKTPFSSIKELIIHQKYKMSEGSYDIALIKLQTPLNYTEFQ

KPICLPSKADTNTIYTNCWVTGWGYTKERGETQNILQKATIPLVPNEECQ

KKYRDYVITKQMICAGYKEGGIDACKGDSGGPLVCKHSGRWQLVGITSWG

EGCARKEQPGVYTKVAEYIDWILEKIQSSKERALETSPA

"Active" or "functional" plasma kallikrein refers to a plasma kallikrein polypeptide or plasma kallikrein polypeptide fragment that retains a biological and/or immunological activity similar, be not necessarily identical to naturally occurring plasma kallikrein, including mature forms. In some embodiments, an active or functional plasma kallikrein is a plasma kallikrein polypeptide or plasma kallikrein polypeptide fragment that binds to C1-INH.

(ii) Factor XII

Factor XII is a serum glycoprotein that participates in the initiation of blood coagulation, fibrinolysis, and the generation of bradykinin and angiotensin. Prekallikrein is cleaved by Factor XII to form kallikrein, which then activates Factor XII resulting in the formation of Factor XIIa and Factor XII fragments (Factor XIIf) ("Histidine-rich glycoprotein binds factor XIIa with high affinity and inhibits contact-initiated coagulation" Macquarrie, et al. Blood 117:4134-4141 2011). C1 inhibitor (C1-INH) has been shown to be an important plasma inhibitor of both Factor XIIa and Factor XIIf ("Effect of negatively charged activating compounds on inactivation of factor XIIa by C1 inhibitor" Pixley, et al. Arch Biochem Biophys 256(2):490-8 1987).

The precursor protein sequence and mRNA sequence of human Factor XII is shown below (accession numbers NM_000505.3 and NP_000496.2), as well as the activated form Factor XIIa.

```
>gi|145275213|ref|NP_000496.2| coagulation factor
XII precursor [Homo sapiens]
                                          (SEQ ID NO: 6)
```
MRALLLLGFLLVSLESTLSIPPWEAPKEHKYKAEEHTVVLTVTGEPCHFP

FQYHRQLYHKCTHKGRPGPQPWCATTPNEDQDQRWGYCLEPKKVKDHCSK

HSPCQKGGTCVNMPSGPHCLCPQHLTGNHCQKEKCEEPQLLRFFHKNEIW

YRTEQAAVARCQCKGPDAHCQRLASQACRTNPCLHGGRCLEVEGHRLCHC

PVGYTGAFCDVDTKASCYDGRGLSYRGLARTTLSGAPCQPWASEATYRNV

TAEQARNWGLGGHAFCRNPDNDIRPWCFVLNRDRLSWEYCDLAQCQTPTQ

AAPPTPVSPRLHVPLMPAQPAPPKPQPTTRTPPQSQTPGALPAKREQPPS

LTR/²NGPLSCGQR/²LRKSLSSMTR/¹VVGGLVALRGAHPYIAALYWGHS

FCAGSLIAPCWVLTAAHCLQDRPAPEDLTVVLGQERRNHSCEPCQTLAVR

SYRLHEAFSPVSYQHDLALLRLQEDADGSCALLSPYVQPVCLPSGAARPS

ETTLCQVAGWGHQPFEGAEEYASFLQEAQVPFLSLERCSAPDVHGSSILPG

MLCAGFLEGGTDACQGDSGGPLVCEDQAAERRLTLQGIISWGSGCGDRNK

PGVYTDVAYYLAWIREHTVS

"/¹ Cleavage at this position (353) leads to full length FXIIa

"/² Cleavage at these additional positions (334 and 343) leads to an active form of FXII known as either β-FXIIa or FXIIf (fragment of FXIIa)

"Active" or "functional" Factor XII refers to a Factor XII polypeptide or Factor XII polypeptide fragment that retains a biological and/or immunological activity similar, be not necessarily identical to naturally occurring Factor XII, including mature forms. In some embodiments, an active or functional Factor XII is a Factor XII polypeptide or Factor XII polypeptide fragment that binds to C1-INH. In some embodiments, active or functional Factor XII is a Factor XIIa polypeptide or a Factor XIIa polypeptide fragment that binds to C1-INH. In some embodiments, active or functional Factor XII is a Factor XIIf polypeptide or a Factor XIIf polypeptide fragment that binds to C1-INH.

C. Detection Agents

Provided methods permit detection of complex formation between a capture reagent, e.g., a capture reagent as disclosed herein, and C1-INH. Detection of the complexes may be achieved by any available method, e.g., an enzyme-linked immunosorbent assay (ELISA). For example, in some embodiments, an antibody to C1-INH is used. In some embodiments, a secondary antibody, e.g., an anti-anti-C1-INH antibody is used. One or more antibodies may be coupled to a detection moiety. In some embodiments, a detection moiety is or comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject's.

In some embodiments, a test is performed by adding capture agent to a substrate, e.g., a reaction vessel, e.g., under conditions such that the capture agent binds to the substrate, e.g., using an ELISA. A sample, e.g., tissue sample from a subject, e.g., blood, plasma, or tears, may be added to the capture-agent containing substrate, e.g., reaction vessel. Any capture agent-binding molecules present may bind to the immobilized capture agent molecules. An antibody or an antibody-detection agent conjugate may be added to the reaction mixture. The antibody part of the conjugate binds to any antigen molecules (e.g., C1-INH) that were bound previously, creating an antibody-antigen-antibody "sandwich". After washing away any unbound conjugate, a substrate solution may be added to aid in detection. For example, after a set interval, the reaction may be stopped (e.g., by adding 1 N NaOH) and the concentration of colored product formed may be measured in a spectrophotometer. The intensity of color is proportional to the concentration of bound antigen.

(i) Antibodies

Antibodies may be used in provided methods. In some embodiments, a capture agent is or comprises an antibody. In some embodiments, a detection agent is or comprises an antibody. In some embodiments, a therapeutic composition for treatment of a pKal-mediated or bradykinin-mediated disorder is or comprises an antibody.

In some embodiments, an antibody specifically binds to a target antigen or epitope, e.g., C1-INH. An antibody that "specifically binds" to an antigen or an epitope is a term well understood in the art, and methods to determine such specific binding are also well known in the art. An antibody is said to exhibit "specific binding" if it reacts or associates more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (e.g., C1-INH) or an antigenic epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding. In some examples, an antibody that "specifically binds" to a target antigen or an epitope thereof may not bind to other antigens or other epitopes in the same antigen.

In some embodiments, an antibody described herein has a suitable binding affinity for a target antigen or antigenic epitope (e.g., C1-INH). As used herein, "binding affinity" refers to the apparent association constant or KA. The KA is the reciprocal of the dissociation constant (KD). The antibody described herein may have a binding affinity (KD) of at least 10-5, 10-6, 10-7, 10-8, 10-9, 10-10 M, or lower. An increased binding affinity corresponds to a decreased KD. Higher affinity binding of an antibody for a first antigen relative to a second antigen can be indicated by a higher KA (or a smaller numerical value KD) for binding the first antigen than the KA (or numerical value KD) for binding the second antigen. In such cases, the antibody has specificity for the first antigen relative to the second antigen. Differences in binding affinity (e.g., for specificity or other comparisons) can be at least 1.5, 2, 3, 4, 5, 10, 15, 20, 37.5, 50, 70, 80, 91, 100, 500, 1000, 10,000 or 105 fold.

Binding affinity (or binding specificity) can be determined by a variety of methods as described herein.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., have a sequence of a framework of an antibody produced by a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) *Science* 242: 423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, a "humanized" immunoglobulin variable region refers to an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

The inhibition constant (Ki) provides a measure of inhibitor potency; it is the concentration of inhibitor required to reduce enzyme activity by half and is not dependent on enzyme or substrate concentrations. The apparent Ki ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o \left( \frac{(K_{i,app} + I + E) - \sqrt{(K_{i,app} + I + E)^2 - 4 \cdot I \cdot E}}{2 \cdot E} \right) \quad \text{Equation 1}$$

Equation 1

Where v=measured velocity; $v_o$=velocity in the absence of inhibitor; $K_{i,app}$=apparent inhibition constant; I=total inhibitor concentration; and E=total enzyme concentration.

D. Kits

The present disclosure also provides kits for use in evaluating C1-INH that is functional in inhibiting PKal and/or FXII. Such kits can comprise: (a) a capture reagent as described herein, and (b) a detection reagent binding to C1-INH, which is also described herein, e.g., an anti-C1-INH antibody, and optionally, (c) C1-INH. In some embodiments, the capture reagent comprises (i) an active form of Factor XII, or a C1-INH-binding fragment thereof; (ii) an active form of kallikrein, or a C1-INH-binding fragment thereof; or (iii) a combination of (i) and (ii). In some embodiments, the capture reagent is immobilized on a substrate, such as a microplate.

In some embodiments, the kit can comprise instructions for use in accordance with any of the methods described herein. The included instructions can comprise a description of how to use the components contained in the kit for measuring the level of functional C1-INH in a sample, which can be a biological sample collected from a human patient.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of functional C1-INH based on inhibition of PKal and/or FXII. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the present disclosure provides articles of manufacture comprising contents of the kits described above.

Application of Assay Methods in Disease Diagnosis and Prognosis

The assay methods and kits described herein can be applied for evaluation of disease, e.g., diagnosis or prognosis of a disease. Evaluation may include identifying a subject as being at risk for or having a disease as described herein, e.g., a pKal-mediated disorder such as HAE (e.g., type I and/or type II HAE). Evaluation may also include monitoring treatment of a disease, such as evaluating the effectiveness of a treatment for a PKal-mediated disorder such as HAE (e.g., type I and/or type II HAE).

A. Diagnosis

In some embodiments, the assay methods and kits are performed to determine the level of C1-INH in a biological sample (e.g., a blood sample or a plasma sample) collected from a candidate subject (e.g., a human patient suspected of having a PKal-mediated disorder such as HAE). The C1-INH level is then compared to a reference value to determine whether the subject has or is at risk for the PKal-mediated disorder. The reference value can be a control level of C1-INH capable of binding to a capture reagent as described herein (e.g., pKal or FXII). In some embodiments, the control level is a level of C1-INH in a control sample that is capable of binding to a capture reagent, such as a sample (e.g., blood or plasma sample) obtained from a healthy subject or population of healthy subjects, which preferably are of the same species as the candidate subject. As used herein, a healthy subject is a subject that is apparently free of the target disease (e.g., a PKal-mediated disorder such as HAE) at the time the level of C1-INH is measured or has no history of the disease.

The control level can also be a predetermined level. Such a predetermined level can represent the level of functional C1-INH (capable of binding to a capture reagent) in a population of subjects that do not have or are not at risk for the target disease. It may also represent the level of functional C1-INH in a population of subjects that might not be likely to benefit from treatment with a pKal inhibitor.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of functional C1-INH in a control population within a predetermined percentile.

The control level as described herein can be determined by routine technology. In some examples, the control level can be obtained by performing a conventional method (e.g., the same assay for obtaining the level of C1-INH capable of binding to a capture reagent in a test sample as described herein) on a control sample as also described herein. In other examples, levels of C1-INH can be obtained from members of a control population and the results can be analyzed by, e.g., a computational program, to obtain the control level (a predetermined level) that represents the level of C1-INH in the control population.

By comparing the level of C1-INH capable of binding to a capture reagent in a sample obtained from a candidate subject to the reference value as described herein, it can be determined as to whether the candidate subject has or is at risk for the PKal-mediated disease (e.g., HAE). For example, if the level of C1-INH that binds to a capture reagent of the candidate subject deviates from the reference value (e.g., reduced as compared to the reference value), the candidate subject might be identified as having or at risk for the disease, e.g., HAE.

As used herein, "an elevated level or a level above a reference value" means that the level of C1-INH that binds to a capture reagent is higher than a reference value, such as a pre-determined threshold or a level of C1-INH that binds to a capture reagent in a control sample. Control levels are described in detail herein. An elevated level of C1-INH that binds to a capture reagent includes a C1-INH level that is, for example, 1%, 5%, 10%, 20%, 30%, 40%, 50%, 60%, 70%, 80%, 90%, 100%, 150%, 200%, 300%, 400%, 500% or more above a reference value. An elevated level of C1-INH that binds to a capture reagent also includes increasing a phenomenon from a zero state (e.g., no or undetectable C1-INH that binds to a capture reagent in a sample) to a non-zero state (e.g., some or detectable C1-INH that binds to a capture reagent in a sample).

As used herein, "a decreased level or a level below a reference value" means that the level of C1-INH that binds to a capture reagent is lower than a reference value, such as a pre-determined threshold or a C1-INH that binds to a capture reagent in a control sample. Control levels are described in detail herein. An decreased level of C1-INH that binds to a capture reagent includes a C1-INH level that is, for example, 1%, 5%, 10%, 20%, 30%, 40%, 50%, 60%, 70%, 80%, 90%, 100%, 150%, 200%, 300%, 400%, 500% or more lower than a reference value. A decreased level of C1-INH that binds to a capture reagent also includes decreasing a phenomenon from a non-zero state (e.g., some or detectable C1-INH that binds to a capture reagent in a sample) to a zero state (e.g., no or undetectable C1-INH that binds to a capture reagent in a sample).

In some embodiments, the candidate subject is a human patient having a symptom of a pKal-mediated disorder, e.g., those disclosed herein such as HAE. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an anti-histamine therapy, a corticosteroid therapy, or both.

In some embodiments, the disease or condition that involves plasma kallikrein activity is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called erythema *marginatum* during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified. In some embodiments, the assay methods described herein can be applied to diagnose either type I HAE or type II HAE. See Examples below.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. Patient. 2012; 5(2):113-26.

Other exemplary diseases or conditions associated with plasma kallikrein activity include non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

A subject who is identified as having or at risk for a PKal-mediated disorder can be subjected to a treatment such as those described herein.

B. Evaluate Treatment Effectiveness

The assay methods described herein can also be applied to evaluate the effectiveness of a treatment for a PKal-mediated disorder (e.g., HAE). For examples, multiple biological samples (e.g., blood or plasma samples) can be collected from a subject to whom a treatment is performed either before and after the treatment or during the course of the treatment. The levels of functional C1-INH (capable of inhibiting PKal and/or FXII) can be measured by any of the assay methods as described herein. If the level of the functional C1-INH increases after the treatment or over the course of the treatment (the level of functional C1-INH in a later collected sample as compared to that in an earlier collected sample) remains the same or increases, it indicates that the treatment is effective. In some examples, the treatment involves a therapeutic agent, such as a kallikrein binding agent as described herein, a bradykinin B2 receptor antagonist as described herein, or a C1-INH replacement agent as described herein. Examples of the therapeutic agents include, but not limited to, DX-2930 or DX88.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

Treatment

Also described herein is methods for treating a subject having or at risk for a PKal-mediated disorder such as HAE. The subject may have a decreased level of functional C1-INH (capable of inhibiting PKal or FXII) as compared to a reference value (e.g., as described herein), which can be determined by any of the assay methods described herein.

A subject at risk for or suffering from (e.g., having) a pKal-mediated or bradykinin-mediated disorder may be treated with any appropriate therapeutic agent. In some embodiments, provided methods include selecting a treatment for a subject based on the output of the assay. Provided assays permit detection of interactions between functional C1-INH present in a sample and an activated component of the bradykinin pathway, e.g., plasma kallikrein, Factor XIIa, and Factor XIIa, among others. Low levels of such interactions are indicative of low levels of functional C1-INH in a sample. In some embodiments, a treatment, e.g., with a kallikrein binding agent, e.g., with a C1-INH replacement therapeutic agent, is selected for a subject whose sample has less than 90%, less than 85%, less than 80%, less than 75%, less than 70%, less than 65%, less than 60%, less than 55%, less than 55%, less than 50%, less than 45%, less than 40%, less than 35%, less than 30%, less than 25%, less than 20%, less than 15%, less than 10%, or less than 5% of functional CI-INH binding activity as compared to a control sample or reference.

In some embodiments, the method comprises one or both of selecting or administering a therapeutic agent, e.g., a kallikrein binding agent as described herein, e.g., a bradykinin B2 receptor antagonist as described herein, e.g., a C1-INH replacement agent as described herein, for administration to the subject based on the output of the assay.

In some embodiments a plasma kallikrein binding protein or polypeptide is administered to a subject. In some embodiments, the kallikrein binding agent is a kallikrein inhibitor, e.g., peptide, a small molecule inhibitor, a kallikrein antibody, or a fragment thereof. In some embodiments, an antagonist of bradykinin B2 receptor is administered to a subject. In some embodiments, a C1-INH replacement therapeutic agent is administered to a subject.

The therapeutic agent, e.g., kallikrein inhibitor, e.g., bradykinin B2 receptor antagonist, e.g., C1-INH replacement agent, may be administered along with another therapy as part of a combination therapy for treatment of the disease or condition that involves plasma kallikrein and/or bradykinin activity. Combination therapy, e.g., with one or more of a kallikrein inhibitor, bradykinin B2 receptor antagonist, or C1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Plasma Kallikrein Binding Agents

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE). In some embodiments a plasma kallikrein binding protein or polypeptide is administered to a subject at risk or suffering from a pKal-mediated or bradykinin-mediated disorder.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least eighty one Kunitz domain sequences are known. Known human homologues include three Kunitz domains of LACI also known as tissue factor pathway inhibitor (TFPI) (Wun et al., (1988) J. Biol. Chem. 263(13):6001-6004; Girard et al., (1989) Nature, 338:518-20; Novotny et al, (1989) J. Biol. Chem., 264(31):18832-18837) two Kunitz domains of Inter-α-Trypsin Inhibitor, APP-I (Kido et al., (1988) J. Biol. Chem., 263(34):18104-18107), a Kunitz domain from collagen, three Kunitz domains of TFPI-2 (Sprecher et al., (1994) PNAS USA, 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa (amino acid sequence in Table 1) containing three Kunitz domains.

TABLE 1

Exemplary Natural Kunitz Domains

```
LACI:         1    MIYTMKKVHA LWASVCLLLN LAPAPLNAds eedeehtiit dtelpplklM
(SEQ ID      51    HSFCAFKADD GPCKAIMKRF FFNIFTRQCE EFIYGGCEGN QNRFESLEEC
NO. 7)      101    KKMCTRDnan riikttlqqe kpdfCfleed pgiCrgyitr yfynnqtkqC
            151    erfkyggClg nmnnfetlee CkniCedgpn gfqvdnygtq lnavnnsltp
            201    qstkvpslfe fhgpswCltp adrglCrane nrfyynsvig kCrpfkysgC
            251    ggnennftsk geClraCkkg fiqriskggl iktkrkrkkq rvkiayeeif
            301    vknm
                   The signal sequence (1-28) is uppercase and underscored
                   LACI-K1 (50-107) is uppercase
                   LACI-K2 (121-178) is underscored
                   LACI-K3 (211-270) is bold BPTI               1          2          3          4          5
(SEQ ID            12345678901234567890123456789012345678901234567890123456789012345678
NO: 8)             RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins containing exemplary Kunitz domains include the following, with SWISS-PROT Accession Numbers in parentheses:

| | | | | | | | |
|---|---|---|---|---|---|---|---|
| A4_HUMAN | (P05067), | A4_MACFA | (P53601), | A4_MACMU | (P29216), | | |
| A4_MOUSE | (P12023), | A4_RAT | (P08592), | A4_SAISC | (Q95241), | | |
| AMBP_PLEPL | (P36992), | APP2_HUMAN | (Q06481), | APP2_RAT | (P15943), | | |
| AXP1_ANTAF | (P81547), | AXP2_ANTAF | (P81548), | BPT1_BOVIN | (P00974), | | |
| BPT2_BOVIN | (P04815), | CA17_HUMAN | (Q02388), | CA36_CHICK | (P15989), | | |
| CA36_HUMAN | (P12111), | CRPT_BOOMI | (P81162), | ELAC_MACEU | (O62845), | | |
| ELAC_TRIVU | (Q29143), | EPPI_HUMAN | (O95925), | EPPI_MOUSE | (Q9DA01), | | |
| HTIB_MANSE | (P26227), | IBP_CARCR | (P00993), | IBPC_BOVIN | (P00976), | | |
| IBPI_TACTR | (P16044), | IBPS_BOVIN | (P00975), | ICS3_BOMMO | (P07481), | | |
| IMAP_DROFU | (P11424), | IP52_ANESU | (P10280), | ISC1_BOMMO | (P10831), | | |
| ISC2_BOMMO | (P10832), | ISH1_STOHE | (P31713), | ISH2_STOHE | (P81129), | | |
| ISIK_HELPO | (P00994), | ISP2_GALME | (P81906), | IVB1_BUNFA | (P25660), | | |
| IVB1_BUNMU | (P00987), | IVB1_VIPAA | (P00991), | IVB2_BUNMU | (P00989), | | |
| IVB2_DABRU | (P00990), | IVB2_HEMHA | (P00985), | IVB2_NAJNI | (P00986), | | |
| IVB3_VIPAA | (P00992), | IVBB_DENPO | (P00983), | IVBC_NAJNA | (P19859), | | |
| IVBC_OPHHA | (P82966), | IVBE_DENPO | (P00984), | IVBI_DENAN | (P00980), | | |
| IVBI_DENPO | (P00979), | IVBK_DENAN | (P00982), | IVBK_DENPO | (P00981), | | |
| IVBT_ERIMA | (P24541), | IVBT_NAJNA | (P20229), | MCPI_MELCP | (P82968), | | |
| SBPI_SARBU | (P26228), | SPT3_HUMAN | (P49223), | TKD1_BOVIN | (Q28201), | | |
| TKD1_SHEEP | (Q29428), | TXCA_DENAN | (P81658), | UPTI_PIG | (Q29100), | | |
| AMBP_BOVIN | (P00978), | AMBP_HUMAN | (P02760), | AMBP_MERUN | (Q62577), | | |
| AMBP_MESAU | (Q60559), | AMBP_MOUSE | (Q07456), | AMBP_PIG | (P04366), | | |
| AMBP_RAT | (Q64240), | IATR_HORSE | (P04365), | IATR_SHEEP | (P13371), | | |
| SPT1_HUMAN | (O43278), | SPT1_MOUSE | (Q9R097), | SPT2_HUMAN | (O43291), | | |
| SPT2_MOUSE | (Q9WU03), | TFP2_HUMAN | (P48307), | TFP2_MOUSE | (O35536), | | |
| TFPI_HUMAN | (P10646), | TFPI_MACMU | (Q28864), | TFPI_MOUSE | (O54819), | | |
| TFPI_RABIT | (P19761), | TFPI_RAT | (Q02445), | YN81_CAEEL | (Q03610) | | |

A variety of methods can be used to identify a Kunitz domain from a sequence database. For example, a known amino acid sequence of a Kunitz domain, a consensus sequence, or a motif (e.g., the PROSITE® Motif) can be searched against the GenBank sequence databases (National Center for Biotechnology Information, National Institutes of Health, Bethesda MD), e.g., using BLAST®; against Pfam database of HMMs (Hidden Markov Models) (e.g., using default parameters for Pfam searching; against the SMART® database; or against the PRODOM® database. For example, the Pfam Accession Number PF00014 of Pfam Release 9 provides numerous Kunitz domains and an HMM for identify Kunitz domains. A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314. The SMART® database (Simple Modular Architecture Research Tool, EMBL, Heidelberg, DE) of HMMs as described in Schultz et al. (1998), Proc. Natl. Acad. Sci. USA 95:5857 and Schultz et al. (2000) Nucl. Acids Res 28:231. The SMART® database contains domains identified by profiling with the hidden Markov models of the HMMer2 search program (R. Durbin et al. (1998) Biological sequence analysis: probabilistic models of proteins and nucleic acids. Cambridge University Press). The database also is annotated and monitored. The PRODOM® protein domain database consists of an automatic compilation of homologous domains (Corpet et al. (1999), Nucl. Acids Res. 27:263-267). Current versions of PRODOM® are built using recursive PSI-BLAST searches (Altschul et al. (1997) Nucleic Acids Res. 25:3389-3402; Gouzy et al. (1999) Computers and Chemistry 23:333-340.) of the SWISS-PROT 38 and TREMBL protein databases. The database automatically generates a consensus sequence for each domain. PROSITE® lists the Kunitz domain as a motif and identifies proteins that include a Kunitz domain. See, e.g., Falquet et al. Nucleic Acids Res. 30:235-238(2002).

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, a kallikrein binding agent (e.g., binding protein, e.g., polypeptide, e.g., inhibitory polypeptides, e.g., antibody, e.g., inhibitory antibody, or other binding agent, e.g., small molecule) binds to the active form of plasma kallikrein. In some embodiments, the kallikrein binding agent, binds to and inhibits plasma kallikrein, e.g., human plasma kallikrein and/or murine kallikrein.

Plasma kallikrein binding proteins can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. Plasma kallikrein binding proteins can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding protein is a monoclonal antibody.

In some embodiments, the kallikrein binding protein binds to and inhibits plasma kallikrein, e.g., human plasma kallikrein and/or murine kallikrein. Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. In some embodiments, the plasma kallikrein binding protein is DX-2930. See also US 20120201756, which is incorporated by reference herein.

The heavy chain and light chain variable region sequences of DX-2930 are provided below.

```
DX-2930 Heavy chain variable region:
                                         (SEQ ID NO: 9)
EVQLLESGGGLVQPGGSLRLSCAASGFTFSHYIMMWVRQAPGKGLEWVS
GIYSSGGITVYADSVKGRFTISRDNSKNTLYLQMNSLRAEDTAVYYCAY
RRIGVPRRDEFDIWGQGTMVTVSS DX-2930 Light chain variable region:
                                        (SEQ ID NO: 10)
DIQMTQSPSTLSASVGDRVTITCRASQSISSWLAWYQQKPGKAPKLLIY
KASTLESGVPSRFSGSGSGTEFTLTISSLQPDDFATYYCQQYNTYWTFG
QGTKVEI
```

In some aspects, a kallikrein binding polypeptide (e.g., inhibitory polypeptide) that binds to the active form of plasma kallikrein. Exemplary polypeptide plasma kallikrein agents are disclosed in U.S. Pat. Nos. 5,795,865, 5,994,125, 6,057,287, 6,333,402, 7,628,983, and 8,283,321, 7,064,107, 7,276,480, 7,851,442, 8,124,586, 7,811,991, and U.S. Publication No. 20110086801, the entire contents of each of which is incorporated herein by reference. In some embodiments, the kallikrein binding polypeptide is DX-88 (a non-naturally occurring kallikrein inhibitor, also known as KALBITOR® (ecallantide), SEQ ID NO:11). In some embodiments, the kallikrein inhibitor comprises or consists of an about 58-amino acid as sequence of amino acids 3-60 of SEQ ID NO:11 or the DX-88 polypeptide having the 60-amino acid sequence of SEQ ID NO:11.

```
                                        (SEQ ID NO: 11)
Glu Ala Met His Ser Phe Cys Ala Phe Lys Ala Asp

Asp Gly Pro Cys Arg Ala Ala His Pro Arg Trp Phe

Phe Asn Ile Phe Thr Arg Gln Cys Glu Glu Phe Ile

Tyr Gly Gly Cys Glu Gly Asn Gln Asn Arg Phe Glu

Ser Leu Glu Glu Cys Lys Lys Met Cys Thr Arg Asp
```

In some embodiments, the plasma kallikrein binding protein is EPIKAL-2 (SEQ ID NO:12), which is non-naturally occurring kallikrein inhibitor having a 58 residue amino acid sequence (residues 3-60 of SEQ ID NO:11) and having amino acid substitutions of Ile to Ser at residue 34 and Glu to Gly at residue 39. The sequence of EPIKAL-2 is shown below:

```
EpiKal2:
                                         (SEQ ID NO: 12)
Met His Ser Phe Cys Ala Phe Lys Ala Asp Asp Gly

Pro Cys Arg Ala Ala His Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp
```

In some embodiments, a plasma kallikrein binding protein can have about 85%, 90%, 91%, 92%, 93%, 94%, 95%, 96%, 97%, 98%, 99% or higher sequence identity to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a binding protein described herein. In some embodiments, a plasma kallikrein binding protein can have about 85%, 90%, 91%, 92%, 93%, 94%, 95%, 96%, 97%, 98%, 99% or higher sequence identity in the constant region (e.g., CH1, CH2, CH3, and/or CL1) to a binding protein described herein.

Bradykinin B2 Receptor Antagonists

In some embodiments, a bradykinin B2 receptor antagonist is administered to a subject. Exemplary bradykinin B2 receptor antagonists include Icatibant (FIRAZYR®), which is a peptidomimetic drug containing 10 amino acids which block binding of native bradykinin to the bradykinin B2 receptor.

C1-INH Replacement Agents

In some embodiment, a replacement C1-INH agent is administered to a subject. Exemplary C1-INH replacement agents are publicly available and include, for example, BERINERT®, which is a purified human pasteurized nanofiltered C1-INH concentrate.

C1 inhibitor therapies, as well as other therapies for HAE, are described in Kaplan, A. P., J Allergy Clin Immunol, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. BERINERT® P (CSL Behring), which is pasteurized, was approved by the F.D.A. in 2009 for acute attacks. CINRYZE® (ViroPharma), which is nanofiltered, was approved by the F.D.A. in 2008 for prophylaxis. RHUCIN® (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat H. *Pylori* will decrease abdominal attacks.

Newer treatments attack the contact cascade. Ecallantide (KALBITOR®, DX-88, Dyax) inhibits plasma kallikrein and has been approved in the US. Icatibant (FIRAZYR®, Shire) inhibits the bradykinin B2 receptor, and has been approved in Europe and the US.

Diagnosis of HAE can rely on, e.g., family history and/or blood tests. Laboratory findings associated with HAE types I, II, and III are described, e.g., in Kaplan, A. P., J Allergy Clin Immunol, 2010, 126(5):918-925. In type I HAE, the level of C1 inhibitor is decreased, as is the level of C4, whereas Clq level is normal. In type II HAE, the level of C1 inhibitor is normal or increased; however, C1 inhibitor function is abnormal. C4 level is decreased and Clq level is normal. In type III, the levels of C1 inhibitor, C4, and Clq can all be normal.

C1 inhibitor therapies, as well as other therapies for HAE, are described in Kaplan, A. P., J Allergy Clin Immunol, 2010, 126(5):918-925.

Exemplary treatments for HAE are provided below. Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Purified plasma-derived concentrate of C1 esterase inhibitor BERINERT® P (CSL Behring), which is pasteurized, was approved by the F.D.A. in 2009 for acute attacks. Human C1 esterase inhibitor/CINRYZE® (ViroPharma), which is nanofiltered, was approved by the F.D.A. in 2008 for prophylaxis. RHUCIN® (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat h. *pylori* will decrease abdominal attacks.

Newer treatments attack the contact cascade. Ecallantide (KALBITOR®, DX-88, Dyax) inhibits plasma kallikrein and has been approved in the US. Icatibant (FIRAZYR®, Shire) inhibits the bradykinin B2 receptor, and has been approved in Europe and the US.

Diagnosis of HAE can rely on, e.g., family history and/or blood tests. Laboratory findings associated with HAE types I, II, and III are described, e.g., in Kaplan, A. P., J Allergy Clin Immunol, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal.

The following examples provide further illustration and are not limiting.

Examples

Example 1. Complex ELISA Using Activated Factor XII and/or Plasma Kallikrein for the Quantitation of Functional C1-INH in Plasma It has been demonstrated that a functional abnormality of C1 inhibitor, C1-INH, is present in Type II hereditary angioedema (HAE), which renders the inhibitor ineffective. Type I HAE has low total C1-INH protein levels. Type III HAE is associated with normal levels of C1-INH. ("Enzymatic pathways in the pathogenesis of hereditary angioedema: The role of C1 inhibitor therapy." Kaplan, A., The Journal of Allergy and Clinical Immunology 126(5): 918-25 2010). C1-INH inhibits factor XIIa, factor XII fragment (XIIf), kallikrein, and plasmin. In the absence of C1-INH function, there is marked activation of the bradykinin-forming cascade resulting in severe angioedema. Type I HAE is generally characterized by decreased levels of total C1-INH. Type II HAE is generally characterized by normal to increased levels of C1-INH, however the function of the C1-INH is abnormal. The mechanism causing Type III HAE is less well characterized, and Type III HAE has been predominantly described in female patients.

Hereditary angioedema (HAE) can be diagnosed using an assay, e.g., chromogenic or ELISA assay, for inhibition of the activated first component of complement (e.g., a functional assay for C1 inhibitor). In some case an assay based on C1s capture of C1INH is used. Existing chromogenic HAE diagnostic assays are generally considered preferable, but both methods have limitations. The chromogenic assay is more likely to have an occasional false positive, while the complex ELISA has a negative predictive value of only 62%. Furthermore, a theoretical limitation for existing diagnostic methods is that the inhibitory activity of C1-INH on the activated first component of complement has little relation to the HAE disease etiology.

We have developed methodologies that detect the function of C1 inhibitor as an inhibitor in the pathway of bradykinin formation, which relates directly to the pathogenic role of C1 inhibitor in causing angioedema. Provided assays permit analysis of the ability or inability of C1-INH to inhibit activated factor XII and plasma kallikrein, which cause overproduction of bradykinin, which in turn causes angioedema. The present example describes assays for functional C1-INH by complex ELISA to examine inhibition of either activated factor XII, plasma kallikrein, or both. These assays have excellent sensitivity for the diagnosis of types I and II HAE.

Figure 2:
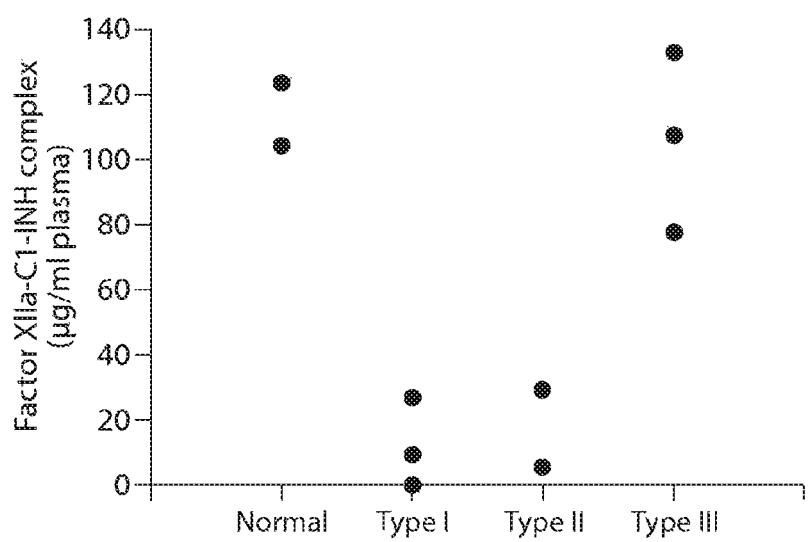
FIG. 2 depicts exemplary detection of activated Factor XII-C1-INH complex formation by ELISA. From left to right—normal control, Type I HAE, Type II HAE and Type III HAE patient plasma samples.
Figure 3:
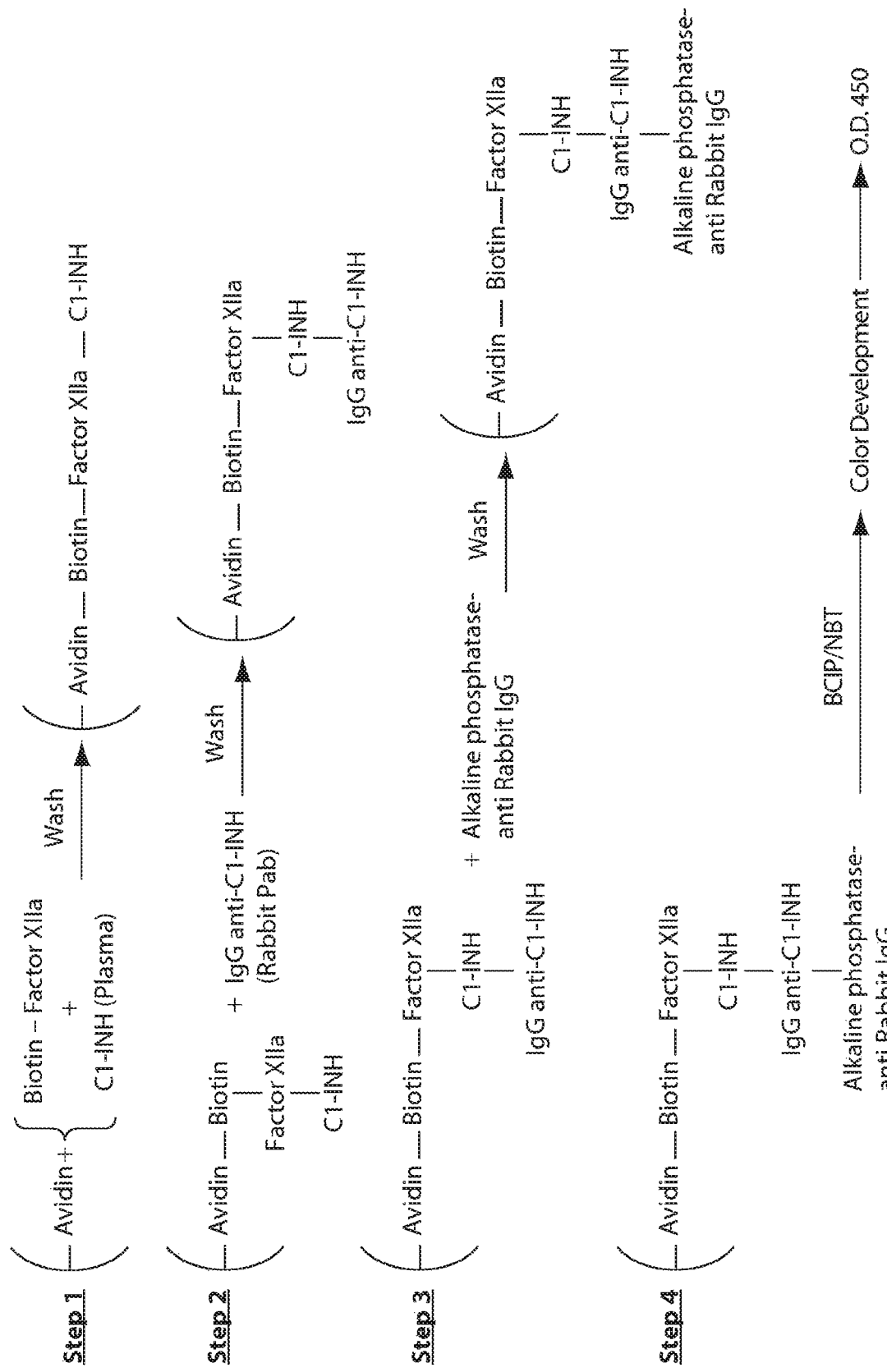
FIG. 3 is a schematic illustration of an exemplary method for measuring C1-INH levels based on inhibition of FXIIa via an ELISA assay.

Our approach was to biotinylate the active enzyme, bind it to an avidin-coated plate, incubate with the plasma (normal for a control, putative HAE plasma as the unknowns), and measure the enzyme-C1-INH complex. We employed alkaline phosphatase labeled antibody to C1-INH for detection of bound C1-INH. For quantification of C1-INH, a standard curve was made by substituting known quantities of C1-INH, in buffer, in place of plasma. Importantly, if other types of angioedema (e.g., Type III HAE) had a mutant C1-INH that inhibits C1s but not activated factor XII or kallikrein, the provided assays would permit detection of the abnormality, whereas the diagnosis would be missed employing either of the currently available assays. About 5% of patients have a normal C4 level even though C1-INH is abnormal. In type II, provided functional assays are important for diagnosis because the C1-INH protein levels are normal. Provided method(s) would be particularly useful in this circumstance. FIGS. 1 and 2 contrast HAE types I and II with two normal controls demonstrating the ease with which the diagnosis can be made. Functional C1-INH has never been measured in patients with type III HAE based on bradykinin-forming enzymes and we demonstrate that it is normal (~40%).

Immulon 2HB plates were coated with 5 μg/ml avidin in coating buffer (100 μl) overnight at 4° C. Plates were washed three times using PBS-Tween (200 μl/each). Subsequently, 200 μl 1% BSA in PBS was added to block the unused sites. The plates were incubated at 37° C. for 1 hr. Plates were washed three times using PBS-Tween (200 μl/each). Added to the plates were: 25 μl standards or samples, 25 μl biotinylated Factor XII1 and/or biotinylated kallikrein (1 μg/ml), and 50 μl binding buffer. Plates were mixed and incubated at 37° C. for 1 hour. Plates were washed three times using PBS-Tween (200 μl/each). A polyclonal antibody to C1-INH was added and incubated at room temperature for 1 hour. Plates were washed three times using PBS-Tween (200 μl/each). Alkaline phosphatase conjugated secondary antibody was added and incubated at room temperature for 1 hour. Plates were washed three times using PBS-Tween (200 μl/each). Substrate for color development was added and incubated at room temperature for 10 minutes. The OD at 450 nm was read and calculations were performed using the standard curve.

As shown in FIGS. 1 and 2, the complex ELISA assays correctly identified Type I and Type II HAE patients with low functional C1-INH as compared to normal controls. One consideration in development of the assay was that it is beneficial to employ an assay that quantitates functional C1-INH based on an enzyme that is requisite for bradykinin formation. The assay may employ one of the activated forms of Factor XII (Factor XIIa or factor XIIf) or plasma kallikrein. Except for C1-INH, Factor XIIa has no other significant inhibitor in plasma. In addition to inhibition by C1-INH, plasma kallikrein is also inhibited by alpha 2 macroglobulin. Nevertheless, complex ELISA assays detecting functional interaction between C1-INH and either Factor XIIa or kallikrein worked well since only that fraction of kallikrein (~60%) that is inhibited by C1-INH is detected.

Example 2. Diagnostic Assay for Hereditary Angioedema Based on Inhibition of Activated Factor XII and/or Plasma Kallikrein Methods Patients and sample collection: The diagnosis of HAE was confirmed by clinical presentation, low C1-INH protein and/or functional level (using the commercial assay). Citrated plasma from 42 patients with HAE and 23 healthy controls was separated by centrifugation of freshly collected blood at 2000 rpm for 10 minutes at 4° C. All samples were immediately aliquoted and stored at −80° C. Samples were handled similarly at all participating sites (Odense, Denmark; Budapest, Hungary) and shipped overnight on dry ice. The protocol was approved by Ethics Committee and Data Protection Agency at both participating sites.

Purified human Factor XIIa and Kallikrein were obtained from Enzyme Research Laboratories (South Bend, IN), biotinylation reagent was obtained from Thermo Scientific (Rockford, IL), and all other reagents were obtained from Sigma chemical company (St. Louis, MO).

Biotinylation of proteins: The proteins were biotinylated according to the manufacturer's recommendations. Briefly, one mg of protein (kallikrein or factor XII) was dissolved in 0.5 ml of phosphate-buffered saline (PBS). About 27 µl of freshly prepared 10 mM Sulfo-NHS-LC-Biotin was added to the protein solution and incubated on ice for two hours. Excess non-reacted and hydrolyzed biotin was removed using a spin-desalting column. The labeling of the proteins were confirmed by ELISA and the protein concentration was determined by Bradford assay (8).

ELISA for the quantitative determination of C1-INH in plasma: Immulon 2HB plates were coated with 5 µg/ml polyclonal antibody to C1-INH. After blocking with 1% BSA in PBS, samples and standards were added and incubated at room temperature for 1 h. Bound C1-INH was probed with alkaline phosphatase conjugated monoclonal antibody to C1-INH followed by color development using 5-bromo-4-chloroindolyl phosphate/nitroblue tetrazolium (BCIP/NBT).

Quantitation of functional C1-INH in plasma based on inhibition of kallikrein and factor XII: Immulon 2HB plates were coated with 5 µg/ml avidin in coating buffer (100 µl) overnight at 4° C. Plates were washed three times using PBS-Tween (200 µl/each). Subsequently, 200 µl 1% BSA in PBS was added to block the unused sites. The plates were incubated at 37° C. for 1 hr and were washed three times using PBS-Tween (200 µl/each). Samples or standards were added to the plates along with biotinylated protein (25 µl standards or samples, 25 µl biotinylated Factor XII or biotinylated kallikrein (1 µg/ml), and 50 µl binding buffer) and were mixed and incubated at 37° C. for 1 hour. After incubation plates were again washed three times using PBS-Tween (200 µl/each) and a polyclonal antibody to C1-INH was added and incubated at room temperature for 1 hour. Plates were washed again and alkaline phosphatase conjugated secondary antibody was added and incubated at room temperature for 1 hour followed by color development using phosphatase substrate BCIP/NBT. The OD at 450 nm was read and calculations were performed using the standard curve. The method is summarized step by step in FIG. 1.

Functional ELISA based on inhibition of complement: ELISA kit was purchased from Quidel Corporation for measuring the amount of functional C1-INH. This assay is based on the ability of plasma C1-INH to inhibit activated C1s (complex ELISA). The assay was performed according to manufacturer's protocol.

Results

Diagnosis of HAE by inhibition of C1s: 23 samples from normal controls and 42 samples from patients with either type I or type II HAE were tested using an existing commercial assay (complex ELISA). According to the assay interpretation, "normal" was 68-100% C1-INH while "abnormal" was below 67%. The instructions indicated that samples between 41% and 67% were to be repeated, because they are considered equivocal, but if the repeat value was within these two figures, it was reported as abnormal. Standards were supplied as a percentage of normal i.e. standards were 0%, 23%, 44%, 66% and 88% and unknowns were read off the curve. The normal control samples varied between 80% and 100% while the HAE samples varied between 0 and 81%. The mean and standard deviation for HAE samples was 38 t 17%. The diagnosis in two of the HAE patients would have been missed using this assay.

Figure 4A:
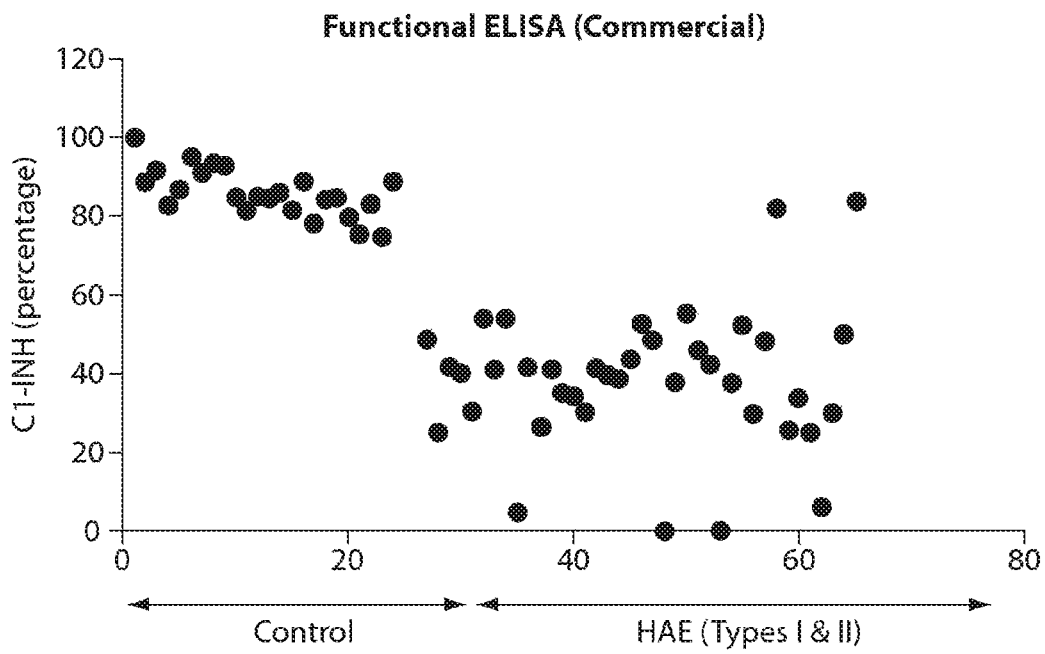
FIGS. 4A-4C include graphs showing data from exemplary functional ELISAs in control samples and HAE samples.
Figure 4B:
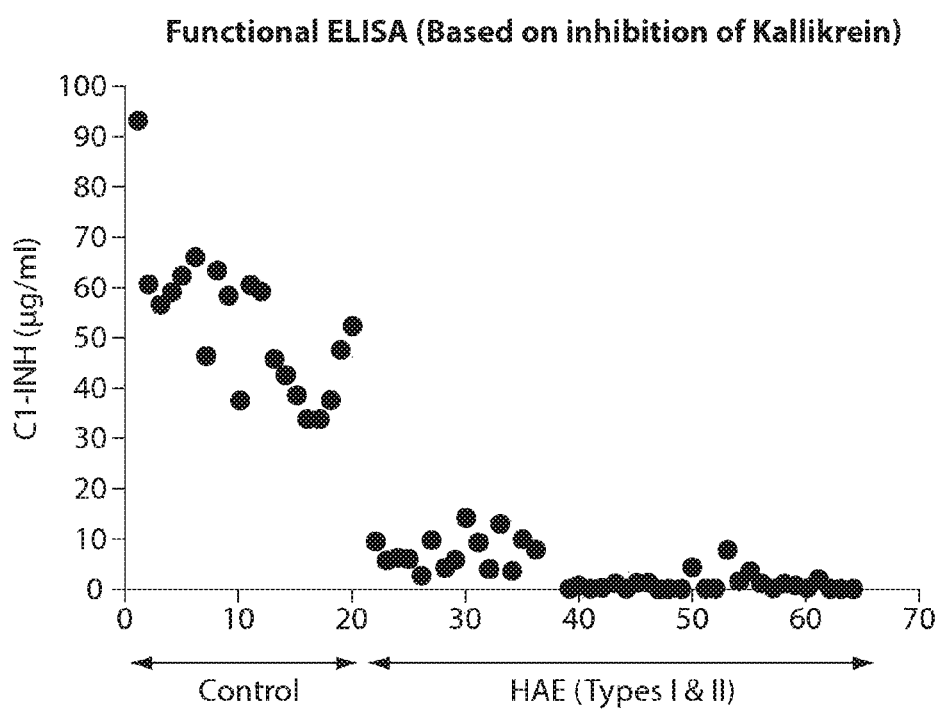
Figure 4C:
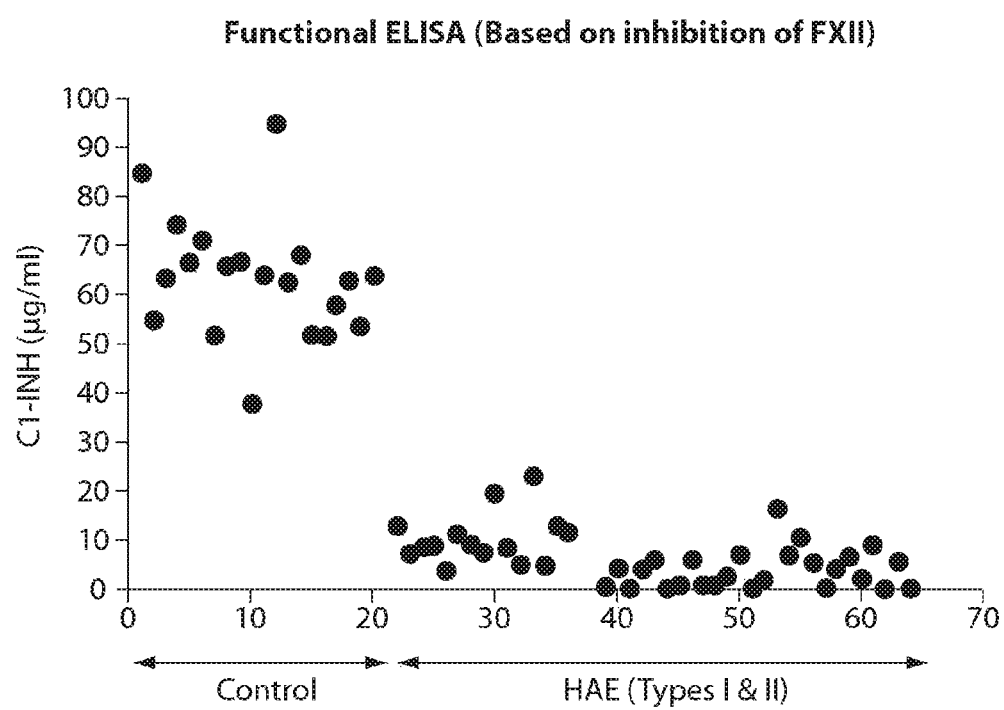

Diagnosis of HAE by inhibition of kallikrein or factor XIIa: The results employing inhibition of plasma kallikrein or inhibition of factor XIIa expressed as mg/ml of complex formation are shown in FIGS. 4B and 4C, respectively, where normal controls were compared to samples obtained from patients with types I and II HAE. The mean and standard deviation for factor XIIa-C1-INH in µg/ml were: normal, 63.1+12.4; and types I and II HAE, 6.1+5.4. The "P" value comparing types I and II HAE to normal controls was <0.0001. The results obtained assaying for kallikrein-C1-INH complexes were strikingly similar with no overlap between the HAE and control groups.

The results herein show that the assays based on the inhibition of kallikrein or factor XIIa correctly identified all of the type I and type II HAE patients tested, which showed a lower level of functional C1-INH as compared to normal controls (FIGS. 3 and 4A-4C). Thus, the assay methods described herein are significantly sensitive as compared to conventional methods in determining the level of functional C1-INH and identifying patients having a PKal-mediated disease (e.g., HAE) based on the level of C1-INH that is functional in inhibiting PKal and/or FXII.

The approach used herein was to biotinylate the active enzyme, bind it to an avidin-coated plate, incubate with the plasma (normal for a control, putative HAE plasma as the unknowns), and measure the enzyme-C1-INH complex. Alkaline phosphatase labeled antibody to C1-INH was used for detection of bound C1-INH. For quantification of C1-INH, a standard curve was made by substituting known quantities of C1-INH, in buffer, in place of plasma. Further, if other types of angioedema (type III HAE for example) had a mutant C1-INH that inhibits C1s but not activated factor XII or kallikrein, this abnormality could be detected using this method whereas the diagnosis would be missed employing either of the currently available assays. The herein described assays have the possibility to supplant the current commercial methods for the diagnosis of types I and II HAE since both assays appear to be more sensitive for detection of dysfunctional C1-INH than inhibition of C1s and could also be used to evaluate patients where an equivocal result is obtained employing other methodology. About 5% of patients have a normal C4 level when asymptomatic, even though C1-INH is abnormal, and in type II HAE patients diagnosis would be dependent on a functional assay since the protein level is typically normal or even elevated. The assays described herein would be particularly useful in this circumstance. In conclusion, diagnosis of HAE types I and II can be ascertained by inhibition of enzymes of the bradykinin-forming cascade so that the diagnosis is made by functional assessment directly related to the abnormality leading to angioedema.

REFERENCES

1. Frank M M, Gelfand J A, Atkinson J P. Hereditary angioedema: the clinical syndrome and its management. Ann Intern Med, 1976; 84: 580-593.
2. Zuraw, B. Clinical practice. Hereditary angioedema. New Eng J Med, 2008; 359: 1027-1036.
3. Wagenaar-Bos I G A et al. Functional C1-inhibitor diagnostics in hereditary angioedema: assay evaluation and recommendations. J Immunol Methods, 2008; 338: 14-20.
4. Kaplan A P, Joseph K. The bradykinin-forming cascade and its role in hereditary angioedema. Ann Allergy, Asthma & Immunol, 2010; 104: 193-204.

5. Gigli, I., Mason, J. W., Colman, R. W., & Austen, K. F. (1970). Interaction of plasma kallikrein with the C1 inhibitor. Journal of Immunology, 104(3), 574-581.
6. Kaplan A P, Joseph K. Kinin formation in C1 inhibitor deficiency. J Allergy Clin Immunol, 2010; 125: 1411-1412.
7. Ziccardi, R. J. (1982). Spontaneous activation of the first component of human complement (C1) by an intramolecular autocatalytic mechanism. Journal of Immunology, 128(6), 2500-2504.
8. Bradford M M. A Rapid and Sensitive Method for the Quantitation of Microgram Quantities of Protein Utilizing the Principle of Protein-Dye Binding. Analyt. Biochem. 1976; 72: 248-254.
9. Tarzi M D, Hickey A, Forster T, Mohammadi M, Longhurst H J. An evaluation of tests used for the diagnosis and monitoring of C1 inhibitor deficiency: normal serum C4 does not exclude hereditary angio-oedema. Clin Exp Immunol. 2007; 149: 513-516.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating a subject having a plasma kallikrein (pKal)-mediated disorder, the method comprising:
    (i) contacting a sample obtained from the subject containing plasma protease C1 inhibitor (C1-INH) with a capture reagent; wherein the capture reagent comprises:
        a) an active form of Factor XII, or a C1-INH binding fragment thereof,
        b) an active form of pKal, or a C1-INH binding fragment thereof, or
        c) a combination of a) and b);
    (ii) measuring a level of the C1-INH in the sample that binds to the capture reagent,
    (iii)—identifying the subject as having a pKal-mediated disorder, wherein the level of the C1-INH obtained in step (i) being reduced relative to the level of the C1-INH in a healthy subject is indicative of occurrence of the pKal-mediated disorder; and
    (iv) administering an effective amount of a therapeutic agent to the subject identified in step (iii);
    wherein the therapeutic agent is a plasma kallikrein inhibitor, a bradykinin B2 receptor antagonist or a C1-INH replacement agent; and
    wherein the pKal-mediated disorder is selected from the group consisting of rheumatoid arthritis, Crohn's disease, brain ischemia/reperfusion injury, cerebral edema, macular edema, arterial or venous thrombosis, thrombosis associated with ventricular assist devices or stents, heparin-induced thrombocytopenia with thrombosis, thromboembolic disease, intestinal bowel disease, and hereditary angioedema (HAE).

2. The method of claim 1, wherein the active form of pKal retains protease activity of a naturally occurring pKal and the active form of Factor XII retains blood coagulation activity of a naturally occurring Factor XII.

3. The method of claim 1, wherein the C1-INH binding fragment of Factor XII or the C1-INH binding fragment of pKal is prepared by
    (a) generating fragments of the full length Factor XII or the full length plasma kallikrein, and
    (b) selecting therefrom a fragment of the full length Factor XII or a fragment of the full length plasma kallikrein that binds C1-INH.

4. The method of claim 1, wherein the capture reagent is immobilized on a substrate.

5. The method of claim 1, wherein the sample is a blood sample or a plasma sample.

6. The method of claim 1, wherein the level of the C1-INH is measured using a detection agent that binds C1-INH.

7. The method of claim 6, wherein the detection agent is an antibody that binds C1-INH.

8. The method of claim 1, wherein the level of the C1-INH is measured by an immunoassay.

9. The method of claim 8, wherein the immunoassay is a Western blot assay, an enzyme linked immunosorbent assay (ELISA), a radioimmunoassay, or an electrochemiluminescence-based detection assay.

10. The method of claim 1, wherein the pKal-mediated disorder is hereditary angioedema (HAE).

11. The method of claim 1, wherein the pKal inhibitor is an anti-pKal antibody.

12. The method of claim 11, wherein the anti-pKal antibody is DX-2930.

13. The method of claim 1, wherein the pKal inhibitor is DX-88 or EPIKAL-2.

14. The method of claim 1, further comprising evaluating effectiveness of the therapeutic agent based on the levels of the C1-INH, wherein an increase of the C1-INH level after the administering of the therapeutic agent or over the course of the administering of the therapeutic agent indicates that the therapeutic agent is effective.

15. The method of claim 1, wherein the subject is resistant to an anti-histamine therapy, a corticosteroid therapy, or both.

16. The method of claim 1, wherein the subject has a symptom of the pKal-mediated disorder.

17. The method of claim 16, wherein the symptom is edema; recurrent attacks of swelling; swelling wherein said swelling is completely or predominantly peripheral; hives; redness, pain, and swelling in the absence of evidence of infection; or non-histamine-mediated edema.

18. The method of claim 1, wherein the subject has no symptoms of the pKal-mediated disorder at the time the sample is collected, has no history of symptoms of the pKal-mediated disorder, or no history of the pKal-mediated disorder.

19. The method of claim 1, wherein the active form of Factor XII is of a naturally-occurring Factor XII and the active form of plasma kallikrein is of a naturally-occurring plasma kallikrein.

20. A method for treating a subject having a plasma kallikrein (pKal)-mediated disorder, the method comprising administering to the subject an effective amount of a therapeutic agent,
    wherein the subject has a reduced level of plasma protease C1 inhibitor (C1-INH) that is capable of binding to a capture reagent as compared to a reference value, and
    wherein the capture reagent comprises:
        i) an active form of Factor XII, or a C1-INH-binding fragment thereof;
        ii) an active form of pKal, or a C1-INH-binding fragment thereof, or
        iii) a combination of i) and ii);

wherein the therapeutic agent is a plasma kallikrein inhibitor, a bradykinin B2 receptor antagonist or a C1-INH replacement agent; and wherein the pKal-mediated disorder is selected from the group consisting of rheumatoid arthritis, Crohn's disease, brain ischemia/reperfusion injury, cerebral edema, macular edema, arterial or venous thrombosis, thrombosis associated with ventricular assist devices or stents, heparin-induced thrombocytopenia with thrombosis, thromboembolic disease, intestinal bowel disease, and hereditary angioedema (HAE).

* * * * *